(12) United States Patent
Gopal

(10) Patent No.: US 9,029,141 B2
(45) Date of Patent: *May 12, 2015

(54) GENERATION OF PATIENT-SPECIFIC DIFFERENTIATED CELL TYPES BY EPIGENETIC INDUCTION

(76) Inventor: Thiru V. Gopal, North Potomac, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 13/064,782

(22) Filed: Apr. 14, 2011

(65) Prior Publication Data

US 2011/0243895 A1  Oct. 6, 2011

Related U.S. Application Data

(63) Continuation-in-part of application No. PCT/US2009/005807, filed on Oct. 26, 2009.

(60) Provisional application No. 61/197,668, filed on Oct. 29, 2008.

(51) Int. Cl.
  *C12N 5/00*   (2006.01)
  *C12N 5/0793*  (2010.01)
  *C12N 5/16*   (2006.01)

(52) U.S. Cl.
  CPC .......... *C12N 5/0619* (2013.01); *C12N 5/16* (2013.01); *C12N 2506/00* (2013.01); *C12N 2501/11* (2013.01); *C12N 2501/115* (2013.01); *C12N 2506/30* (2013.01)

(58) Field of Classification Search
  None
  See application file for complete search history.

(56) References Cited

U.S. PATENT DOCUMENTS

| 2005/0153443 | A1 | 7/2005 | Lanza et al. |
| 2005/0170506 | A1 | 8/2005 | Sayre et al. |
| 2007/0020759 | A1 | 1/2007 | Sayre et al. |

OTHER PUBLICATIONS

Klimanskaya et al (Nature Reviews, 1-12, 2007).*
Singh et al (Gene, 354: 140-6, 2005).*
Trounce et al (Mitochondria in Health and Disease, Edited by Carolyn D, Berdanier, p. 539-558, 2005).*
Briggs, R. and King, TJ, Transplantation of Living Nuclei From Blastula Cells into Enucleated Frogs' Eggs, Proceedings of National Academy of Sciences, U S A, 38: 455-463 (1952).
Gurdon, JB, Adult Frogs Derived From the Nuclei of Single Somatic Cells, Developmental Biology, 4:256-273 (1962).
Gurdon, JB, Nuclear Transplantation in Xenopus, Methods in Molecular Biology, 325:1-9 (2006).
Gurdon, JB and Byrne, JA, The First Half-Century of Nuclear Transplantation, Proceedings of National Academy of Sciences, 100(14):8048-8052 (2003).
Bryne, JA, Pedersen DA, Clepper, LL, Nelson, M, Sanger WG, Gokhale,S., Wolf, DP and Mitalipov, SM, Producing Primate Embryonic Stem Cells by Somatic Cell Nuclear Transfer, Nature, 450(22):497-502 (2007); 3 pages of Supplementary Information online, doi:10.1038/nature06357.
Hochedlinger, K and Jaenisch, R, Monoclonal Mice Generated by Nuclear Transfer from Mature B and T Cells, Nature, 415:1035-1038 (2002).
Wilmut, I, Schnieke, AE, Mc Whir, J, Kind, AJ, and Campbell, HS, Viable Offspring Derived From Fetal and Adult Mammalian Cells, Nature, 387:810-813 (1997).
Aoi, T, Nagakawa, M, Ichisaka, T, Okita, K, Takahashi, K, Chiba, T and Shinya, Y, Science, 321:699-702 (2008), including 2 pages of Erratum, www.sciencemag.org (2008).
Lowry,WE, Richter, L, Yachechko,R, Pyle, AD, Tchieu, J, Sridharan, R, Clark, AT, and Plath, K, Generation of Human Induced Pluripotent Stem Cells from Dermal Fibroblasts, Proceedings of National Academy of Sciences (U.S.A.), 105(8):2883-2888 (2008).
Meissner, A, Wernig, M and Jaenisch, R, Direct Reprogramming of Genetically Unmodified Fibroblasts Into Pluripotent Stem Cells, Nature Biotechnology, 25(10):1177-1181 (2007).
Nakagawa, M, Koyanagi, M, Tanabe, K, Takahashi, K, Ichisaka, T, Aoi, T, Okita, K, Mochiduki, Y, Takizawa, N, and Yamanaka, S, Gneration of Induced Pluripotent Stem Cells With Myc From Mouse and Human Fibroblasts, Nature Biotechnology, 26(1):101-106 (2008).
Takahashi, K, Tanabe, K, Ohnuki, M, Narita, M, Ichisaka, T, Tomoda, K, and Yamanaka S, Induction of Pluripotent Stem Cells from Adult Human Fibroblasts by Defined Factors, Cell, 131:1-12(2007).
Takahashi, K and Yamanaka, S, Induction of Pluripotent Stem Cells from Mouse Embryonic and Adult Fibroblast Cultures by Defined Factors, Cell, 126:663-676 (2006).
Yamanaka, S, Induction of Pluripotent Stem Cells from Mouse Fibroblasts by Four Transcription Factors, Cell Proliferation, 41(Supplement 1):51-56 (2008).
Yu, J, Vodyanik, MA, Smuga-Otto, K, Antosiewicz-Bourget, J, Frane, JL, Tian, S, Nie,J, Jonsdottir, GA, Ruoiti, V, Stewart, R, Slukvin, II,and Thomson, JA, Induced Pluripotent Stem Cell Lines Derived from Human Somatic Cells, Science, 318:1917-1920 (2007).
Cowan, CA, Atienza, J, Melton, DA,and Eggan, K, Nuclear Reprogramming of Somatic Cells After Fusion With Human Embryonic Stem Cells, Science, 309:1369-1373 (2005).

(Continued)

*Primary Examiner* — Peter Paras, Jr.
*Assistant Examiner* — Magdalene Sgagias
(74) *Attorney, Agent, or Firm* — Jyoti C Iyer

(57) ABSTRACT

Disclosure of a mammalian cytoplasmic donor cell line. Disclosure of a patient specific cell line. Methods to obtain a mammalian cytoplasmic donor cell line by fusing a differentiated mammalian cell and a functionally enucleated mammalian embryonic cell line. Methods to obtain a mammalian cytoplasmic donor cell line by fusing a differentiated mammalian cell and a functionally enucleated human cancer cell. Methods to obtain a patient specific cell line of a cell type similar to a mammalian cytoplasmic donor cell line by functionally enucleating the mammalian cytoplasmic donor cell line and fusing the functionally enucleated mammalian cytoplasmic donor cell line with a differentiated cell obtained from the patient. A method of treatment of a human patient by administering the patient-specific cell line to the patient.

9 Claims, 12 Drawing Sheets

(56) References Cited

OTHER PUBLICATIONS

Davis, FM and Sdelberg, EA, Use of Somatic Cell Hybrids for Analysis of the Differentiated State, Bacteriological Reviews, 37(2):197-214 (1973).

Wright, WE and Aronoff, J, The Suppression of Myogenic Functions in Heterokaryons Formed by Fusing Chick Myocytes to Diploid Rat Fibroblasts, Cell Differentiation, 12:299-306 (1983).

Tada M, Takahama, Y, Abe, K, Nakatsuji, N and Tada, T, Nuclear Reprogramming of Somatic Cells by In Vitro Hybridization with ES Cells, Current Biology, 11:1553-1558 (2001).

Terranova, R, Pereira, CF, Du Roure, C, Merkenschlager, M, and Fisher, AG, Acquistion and Extinction of Gene Expression Programs are Separable Events in Heterokaryon Reprogramming, Journal of Cell Science, 119:2065-2072 (2006).

Baron, MH, and Maniatis, T, Rapid Reprogramming of Globin Gene Expression in Transient Heterokaryons, Cell, 46:591-602 (1986).

Blau, H, Chiu, C-P, and Webster, C, Cytoplasmic Activation of Human Nuclear Genes in Stable Heterocaryons, Cell, 32:1171-1180 (1983).

Pereira, CF, Terranova, R, Ryan, NK, Santos, J, Morris, KJ, Cui, W, Merkenschlager, M and Fisher, AG, Heterokaryon-Based Reprogramming of Human B Lymphocytes for Pluripotency requires Oct4 But Not Sox2, PloS Genetics, 4(9): e1000170, doi:10.1371/journal.pgen.1000170, pp. 1-14 (2008).

Wright, WE, The Isolation of Heterokaryons and Hybrids by a Selective System Using Irreversible Biochemical Inhibitors, Experimental Cell Research, 112:395-407(1978).

Wright, WE, Induction of Myosin Ligth Chain Synthesis in Heterokaryons Between Normal Diploid Cells, In Vitro, 18(10): 851-858 (1982).

Bunn, CL, Wallace, DC, and Eisenstadt, JM, Cytoplasmic Inheritance of Chloramphenical Resistance in Mouse Tissue Culture Cells, Proceedings of National Academy of Sciences, USA, 71(5):1681-1685 (1974).

Gopalakrishnan, TV and Anderson WF, Epigenetic Activation of Phenylalanine Hydroxylase in Mouse Erythroleukemia Cells by the Cytoplast of Rat Hepatoma Cells, Proceedings of National Academy of Sciences, USA, 76(8):3932-3936 (1979).

Gopalakrishnan, TV, Thompson, EB, and Anderson WF, Extinction of Hemoglobin Inducibility in Friend Erythroleukemia Cells by Fusion with Cytoplasm of Enucleated Mouse Neuroblastoma or Fibroblast Cells, Proceedings of National Academy of Sciences, 74(4):1642-1646 (1977).

Gopalakrishnan, TV, and Littlefield, JW, RNA from Rat Hepatoma Cells Can Activate Phenylalanine Hydroxylase Gene of Mouse Erythroleukemia Cells, Somatic Cell Genetics, 9(1):121-131 (1983).

Kuehn, MR, Bradley, A, Robertson, EJ, and Evans, JE, A potential Animal Model for Lesch-Nyhan Syndrome Through Introduction of HPRT Mutations into Mice, Nature, 326:295-298 (1987).

Huangfu, D, Osafune, K, Maehr, E, Guo, W, Eijkelenboom, Chen S, Muhlestein, W and, Melton, DA, Induction of Pluripotent Stem Cells From Primary Human Fibroblasts with only Oct4 and Sox 2, Nature Biotechnology, 26(11):1269-1275 (2008).

Shiroi, A, Yoshikawa, M, Yokota, H, Fukui, H, Ishizaka, S, Tatsumi, K, and Takahashi, Y, Identification of Insulin-Producing cells Derived from Embryonic Stem Cells by Zinc-Chelating Dithizone, Stem Cells, 20:284-292 (2002).

Breakefield, XO, and Nirenberg, MW, Selection for Neuroblastoma Cells That Synthesize Certain Transmitters, Proceedings of National Academy of Sciences, USA, 7I(6):2530-2533 (1974).

Hagerty, DF, Young, PL, and Buese, JV, A Tyrosine-Free Medium for the Selective Growth of Cells Expressing Phenlyalanine Hydroxylase Activity, Developmental Biology, 44:158-168 (1975).

One page of International Search Report in PCT/US2009/05807 dated Feb. 12, 2010.

Pritsos, CA, Briggs, LA, and Gustafson, DL, A New Cellular Target for Mitomycin C: A case for mitochondrial DNA, Oncology Research, 9:333-337(1997), Cognizant Comm. Corp.

Dreesen, O and Brivanlou AH, Signalling Pathways in Cancer and Embryonic Stem Cells, Stem Cell Rev. 1-11(2007), DOI 10.1007/s/12015-007-0004-8, Humana Press 2007.

Kim, J and Orkin, SH, Embryonic stem cell-specific signatures in cancer: insights into genomic regulatory networks and implications for medicine, Genome Medicine, 3(75)1-8(2011), BioMed Central.

Do, JT and Scholer, HR, Nuclei of Embryonic Stem Cells Reprogram Somatic Cells, Stem Cells,22:941-949 (2004).

Strelchenko N, Kukharenko V, Schkumatov A, Verlinsky O, Kuliev A, Verlinsky Y, Reprogramming of Human Somatic Cells by Embryonic Stem Cell Cytoplast, Reproductive BioMedicine Online, 12(1):107-111(2006); www.rbmonline.com/Article/2071 on web Nov. 18, 2005.

* cited by examiner

| Genome Loci | HFL-140 Cytoplasmic donor | 4299 Human fibroblast | EIH-1Fb derived from 4299 | PCA1584 PBMNC | EIH-4 Derived fromPCA 1584 |
|---|---|---|---|---|---|
| Amelogenin | X | X Y | X Y | X Y | X Y |
| vWA | 18 | 14 16 | 14 16 | 17 18 | 17 18 |
| D8S1179 | 11 13 | 10 15 | 10 15 | 14 | 14 |
| TPOX | 11 | 8 | 8 | 8 11 | 8 11 |
| FGA | 23 24 | 19 | 19 | 19 20 | 19 20 |
| D3S1358 | 16 | 14 16 | 14 16 | 15 17 | 15 17 |
| THO1 | 7 8 | 9.3 10 | 9.3 10 | 7 9 | 7 9 |
| D21S11 | 30 | 30 30.2 | 30 30.2 | 30 31.2 | 30 31.2 |
| D18S51 | 12 16 | 16 | 16 | 13 17 | 13 17 |
| Penta E | 12 13 | 7 13 | 7 13 | 15 17 | 15 17 |
| D5S818 | 11 14 | 11 | 11 | 10 12 | 10 12 |
| D13S317 | 10 11 | 8 12 | 8 12 | 12 13 | 12 13 |
| D7S820 | 8 11 | 10 11 | 10 11 | 10 | 10 |
| D16S539 | 9 10 | 11 12 | 11 12 | 10 | 10 |
| CSF1PO | 11 12 | 11 | 11 | 10 | 10 |
| Penta D | 12 13 | 9 13 | 9 13 | 9 12 | 9 12 |

FIGURE 5

| Genome Loci | FP-30A Cytoplasmic donor | | 4299 Adult human fibroblast | | EIPB-2Fb Derived from 4299 | | FP-31A Cytoplasmic Donor | | A1749 PBMNC | | EIPB-3 Derived from A1749 | |
|---|---|---|---|---|---|---|---|---|---|---|---|---|
| Amelogenin | X | | X | Y | X | Y | X | Y | X | Y | X | Y |
| vWA | 18 | | 14 | 16 | 14 | 16 | 16 | 17 | 15 | 18 | 15 | 18 |
| D8S1179 | 11 | 13 | 10 | 15 | 10 | 15 | 11 | 13 | 10 | 14 | 10 | 14 |
| TPOX | 11 | | 8 | | 8 | | 11 | 12 | 8 | 11 | 8 | 11 |
| FGA | 23 | 24 | 19 | | 19 | | 20 | 25 | 21.2 | 27 | 21.2 | 27 |
| D3S1358 | 16 | | 14 | 16 | 14 | 16 | 16 | 17 | 13 | 15 | 13 | 15 |
| THO1 | 7 | 8 | 9.3 | 10 | 9.3 | 10 | 6 | 9.3 | 6 | 9 | 6 | 9 |
| D21S11 | 30 | | 30 | 30.2 | 30 | 30.2 | 29 | | 19 | 33.2 | 19 | 33.2 |
| D18S51 | 12 | 16 | 16 | | 16 | | 12 | | 13 | 20 | 13 | 20 |
| Penta E | 12 | 13 | 7 | 13 | 7 | 13 | 10 | 11 | 11 | 13 | 11 | 13 |
| D5S818 | 11 | 14 | 11 | | 11 | | 11 | 13 | 11 | 12 | 11 | 12 |
| D13S317 | 10 | 11 | 8 | 12 | 8 | 12 | 8 | 11 | 12 | 13 | 12 | 13 |
| D7S820 | 8 | 11 | 10 | 11 | 10 | 11 | 9 | | 9 | 10 | 9 | 10 |
| D16S539 | 9 | 10 | 11 | 12 | 11 | 12 | 11 | 13 | 11 | 12 | 11 | 12 |
| CSF1PO | 11 | 12 | 11 | | 11 | | 12 | 13 | 11 | | 11 | |
| Penta D | 12 | 13 | 9 | 13 | 9 | 13 | 9 | 11 | 12 | | 12 | |

FIGURE 10

| Genome Loci | DAN-47A Cytoplasmic donor | 4299 Human Fibroblast | | EIDN-3Fb Derived from 4299 | | A1749 PBMNC | | EIDN-4 Derived from A1749 | |
|---|---|---|---|---|---|---|---|---|---|
| Amelogenin | X | X | Y | X | Y | X | Y | X | Y |
| vWA | 15  18 | 14 | 16 | 14 | 16 | 15 | 18 | 15 | 18 |
| D8S1179 | 13  14 | 10 | 15 | 10 | 15 | 10 | 14 | 10 | 14 |
| TPOX | 8  11 | 8 | | 8 | | 8 | 11 | 8 | 11 |
| FGA | 19  13 | 19 | | 19 | | 21.2 | 27 | 21.2 | 27 |
| D3S1358 | 15 | 14 | 16 | 14 | 16 | 13 | 15 | 13 | 15 |
| THO1 | 8  9 | 9.3 | 10 | 9.3 | 10 | 6 | 9 | 6 | 9 |
| D21S11 | 28  31.2 | 30 | 30.2 | 30 | 30.2 | 19 | 33.2 | 19 | 33.2 |
| D18S51 | 14  17 | 16 | | 16 | | 13 | 20 | 13 | 20 |
| Penta E | 13  14 | 7 | 13 | 7 | 13 | 11 | 13 | 11 | 13 |
| D5S818 | 9  10 | 11 | | 11 | | 11 | 12 | 11 | 12 |
| D13S317 | 10  11 | 8 | 12 | 8 | 12 | 12 | 13 | 12 | 13 |
| D7S820 | 8  12 | 10 | 11 | 10 | 11 | 9 | 10 | 9 | 10 |
| D16S539 | 9  10 | 11 | 12 | 11 | 12 | 11 | 12 | 11 | 12 |
| CSF1PO | 10  13 | 11 | | 11 | | 11 | | 11 | |
| Penta D | 9  12 | 9 | 13 | 9 | 13 | 12 | | 12 | |

FIGURE 14

GENERATION OF PATIENT-SPECIFIC DIFFERENTIATED CELL TYPES BY EPIGENETIC INDUCTION

RELATED APPLICATIONS

This application is a continuation-in-part of co-pending International Application PCT/US2009/005807 filed Oct. 26, 2009, which claims priority from U.S. Application Ser. No. 61/197,668, filed Oct. 29, 2008, which are both incorporated in entirety by reference.

BACKGROUND

It has been well established in a number of biological systems that cytoplasmic regulatory factors play a cardinal role in regulating nuclear gene activity and nuclear reprogramming. Initially it was shown that transfer of nuclei from fully differentiated cells of frog into enucleated frog oocytes resulted in the development of tadpoles to mature frogs [Briggs, R. and T. J. King, Transplantation of Living Nuclei From Blastula Cells into Enucleated Frogs' Eggs. Proc Natl Acad Sci USA, 1952. 38(5): p. 455-63; Gurdon, J. B., Adult frogs derived from the nuclei of single somatic cells. Dev Biol, 1962. 4: p. 256-73; Gurdon, J. B., Nuclear transplantation in Xenopus. Methods Mol Biol, 2006. 325: p. 1-9; Gurdon, J. B. and J. A. Byrne, The first half-century of nuclear transplantation. Biosci Rep, 2004. 24(4-5): p. 545-57.].

Successful generation of embryonic stem (ES) cells of different species by Somatic Cell Nuclear Transfer (SCNT) into enucleated eggs has firmly established that different cell types arise from epigenetic changes and not from any permanent change in the DNA sequence [Byrne, J. A., et al., Producing primate embryonic stem cells by somatic cell nuclear transfer. Nature, 2007. 450(7169): p. 497-502; Hochedlinger, K. and R. Jaenisch, Monoclonal mice generated by nuclear transfer from mature B and T donor cells. Nature, 2002. 415(6875): p. 1035-8; Wilmut, I., et al., Viable offspring derived from fetal and adult mammalian cells. Nature, 1997. 385(6619): p. 810-3.]. Generation of induced Pluripotent Stem (iPS) cells has also shown that epigenetic changes can be brought out by forced expression of a few genes introduced exogenously into adult cells [Aoi, T., et al., Generation of pluripotent stem cells from adult mouse liver and stomach cells. Science, 2008. 321(5889): p. 699-702; Lowry, W. E., et al., Generation of human induced pluripotent stem cells from dermal fibroblasts. Proc Natl Acad Sci USA, 2008. 105(8): p. 2883-8; Meissner, A., M. Wernig, and R. Jaenisch, Direct reprogramming of genetically unmodified fibroblasts into pluripotent stem cells. Nat Biotechnol, 2007. 25(10): p. 1177-81; Nakagawa, M., et al., Generation of induced pluripotent stem cells without Myc from mouse and human fibroblasts. Nat Biotechnol, 2008. 26(1): p. 101-6; Takahashi, K., et al., Induction of pluripotent stem cells from adult human fibroblasts by defined factors. Cell, 2007. 131(5): p. 861-72; Takahashi, K. and S. Yamanaka, Induction of pluripotent stem cells from mouse embryonic and adult fibroblast cultures by defined factors. Cell, 2006. 126(4): p. 663-76; Yamanaka, S., Induction of pluripotent stem cells from mouse fibroblasts by four transcription factors. Cell Prolif, 2008. 41 Suppl 1: p. 51-6; Yu, J., et al., Induced pluripotent stem cell lines derived from human somatic cells. Science, 2007. 318(5858): p. 1917-20.].

Tissue culture cell lines that express functions characteristic of the tissues from which they were established have been used to study the regulation of differentiated functions in vitro. Somatic cell hybrids between different cell types have shown that differentiated functions can either be activated or extinguished in such cell hybrids depending upon the cell types used in these hybrids [Cowan, C. A., et al., Nuclear reprogramming of somatic cells after fusion with human embryonic stem cells. Science, 2005. 309(5739): p. 1369-73; Davis, F. M. and E. A. Adelberg, Use of somatic cell hybrids for analysis of the differentiated state. Bacteriol Rev, 1973. 37(2): p. 197-214; Wright, W. E. and J. Aronoff, The suppression of myogenic functions in heterokaryons formed by fusing chick myocytes to diploid rat fibroblasts. Cell Differ, 1983. 12(5): p. 299-306; Tada, M., et al., Nuclear reprogramming of somatic cells by in vitro hybridization with ES cells. Curr Biol, 2001. 11(19): p. 1553-8; Terranova, R., et al., Acquisition and extinction of gene expression programs are separable events in heterokaryon reprogramming. J Cell Sci, 2006. 119(Pt 10): p. 2065-72.]. Such activation and extinction of differentiated functions were also seen in heterokaryons immediately after cell fusion before formation of synkaryons [Terranova, R., et al., Acquisition and extinction of gene expression programs are separable events in heterokaryon reprogramming. J Cell Sci, 2006. 119(Pt 10): p. 2065-72; Baron, M. H. and T. Maniatis, Rapid reprogramming of globin gene expression in transient heterokaryons. Cell, 1986. 46(4): p. 591-602; Blau, H. M., C. P. Chiu, and C. Webster, Cytoplasmic activation of human nuclear genes in stable heterocaryons. Cell, 1983. 32(4): p. 1171-80; Pereira, C. F., et al., Heterokaryon-based reprogramming of human B lymphocytes for pluripotency requires oct4 but not sox2. PLoS Genet, 2008. 4(9): p. e1000170; Wright, W. E., The isolation of heterokaryons and hybrids by a selective system using irreversible biochemical inhibitors. Exp Cell Res, 1978. 112(2): p. 395-407; Wright, W. E., Induction of myosin light chain synthesis in heterokaryons between normal diploid cells. In Vitro, 1982. 18(10): p. 851-8.], suggesting the role of cytoplasmic regulatory factors responsible for nuclear gene activity.

Other studies investigated the role of cytoplasmic regulatory factors in regulating nuclear gene activity and including development of tools to enucleate cells and form hybrids between such enucleated cells, called cytoplasts, and another whole cell. The resulting cytoplast-whole cell hybrids were called cybrids [Bunn, C. L., D. C. Wallace, and J. M. Eisenstadt, Cytoplasmic inheritance of chloramphenicol resistance in mouse tissue culture cells. Proc Natl Acad Sci USA, 1974. 71(5): p. 1681-5.]. It has been shown that cytoplasmic regulatory factors bring about permanent activation as well as extinction of differentiated functions in somatic cell cybrids, and such factors are cytoplasmically inheritable [Gopalakrishnan, T. V. and W. F. Anderson, Epigenetic activation of phenylalanine hydroxylase in mouse erythroleukemia cells by the cytoplast of rat hepatoma cells. Proc Natl Acad Sci USA, 1979. 76(8): p. 3932-6; Gopalakrishnan, T. V., E. B. Thompson, and W. F. Anderson, Extinction of hemoglobin inducibility in Friend erythroleukemia cells by fusion with cytoplasm of enucleated mouse neuroblastoma or fibroblast cells. Proc Natl Acad Sci USA, 1977. 74(4): p. 1642-6.].

Since cell enucleation was an inefficient process and could not be applied uniformly to different cell types, chemical means were used to enucleate cells functionally rather than physically to totally exclude nuclear gene contribution from cytoplasmic donor cells during this activation process [Gopalakrishnan, T. V. and J. W. Littlefield, RNA from rat hepatoma cells can activate phenylalanine hydroxylase gene of mouse erythroleukemia cells. Somatic Cell Genet, 1983. 9(1): p. 121-31.]. It was shown in these studies that treatment of cells with a high concentration of Mitomycin C completely prevented contribution of single selectable gene marker necessary for the survival of hybrids following fusion with a partner cell deficient in the same selectable marker gene. These studies led to establishing conditions to investigate the role of non genetic components of a cell in regulating nuclear gene activity [Gopalakrishnan, T. V. and J. W. Littlefield, RNA from rat hepatoma cells can activate phenylalanine hydroxylase gene of mouse erythroleukemia cells. Somatic Cell Genet, 1983. 9(1): p. 121-31.]. These were termed as "pseudocybrids." These studies showed that cytoplasmic regulatory factors for a liver specific marker, phenylalanine hydroxylase, exist in liver cell lines that express phenylalanine hydroxylase constitutively, which when introduced into a suitable non-hepatic recipient cell line by formation of cybrids or pseudocybrids, can bring about permanent activation of phenylalanine hydroxylase gene from the genome of the non-hepatic cell [Gopalakrishnan, T. V. and J. W. Littlefield, RNA from rat hepatoma cells can activate phenylalanine hydroxylase gene of mouse erythroleukemia cells. Somatic Cell Genet, 1983. 9(1): p. 121-31.]. The resulting cybrids could be used as cytoplasmic donor cells to epigenetically activate phenylalanine hydroxylase gene in different recipient cells to generate second generation cybrids. These studies also showed that the cytoplasmic activation was brought about by RNA or perhaps a protein coded by it, and that the cytoplasmic regulatory factor was perpetuated continuously in culture.

Epigenetic mechanisms are responsible for development of different cells types from a fertilized egg. Somatic cell nuclear transfer (SCNT) experiments have established that differentiated cell types arise from reversible epigenetic control mechanisms rather than from any permanent alteration in the genetic component. Embryonic stem (ES) cells of various mammalian species have been developed by SCNT into unfertilized eggs. These cells arise from epigenetic changes caused by egg cytoplasm to donor nucleus genome. Recently, ES like cells, referred to as induced pluripotent stem (iPS) cells, have been generated by direct reprogramming of adult cells following introduction of a few specific genes into them. This has opened up opportunities to generate patient-specific iPS cells that can be used to study the disease process, for drug discovery and drug toxicology studies, and for regenerative medicine and cell therapy applications. However, generation of specific cell types either from ES cells or iPS cells as a pure population in sufficient quantity to meet the demand for various applications has thus far remained inefficient.

SUMMARY

The disclosed teachings provide a mammalian cytoplasmic donor cell line having a first self-propagating differentiated cell of a cell-type similar to a first cell, wherein the first cell is a differentiated cell from a mammalian tissue. The mammalian cytoplasmic donor cell line is obtained from fusing the first cell and a functionally enucleated mammalian embryonic stem cell. The functionally enucleated mammalian embryonic stem cell is obtained by functionally enucleating a mammalian embryonic stem cell.

The disclosed teachings provide a functionally enucleated mammalian cytoplasmic donor cell line obtained by functionally enucleating a mammalian cytoplasmic donor cell line.

The disclosed teaching provide a cell line specific to a mammalian patient having a second self-propagating differentiated cell of a cell type similar to the first cell. The cell line specific to the mammalian patient is obtained by fusing a functionally enucleated mammalian cytoplasmic donor cell line and a second cell. The second cell is a cell obtained from the mammalian patient.

The disclosed teachings provide a method of preparing a cell line specific to a mammalian patient. The method includes: obtaining a mammalian embryonic cell; treating the mammalian embryonic cell with a DNA interchelating agent to obtain a functionally enucleated mammalian embryonic cell, treating the functionally enucleated mammalian embryonic stem cell with an agglutinin to obtain an agglutinin-treated functionally enucleated mammalian embryonic stem cell; obtaining a first cell, wherein the first cell is a differentiated cell from a mammalian tissue, obtaining a mammalian cytoplasmic donor cell line having a first self-propagating differentiated cell of a cell type similar to the first cell by fusing the first cell with the agglutinin-treated functionally enucleated mammalian embryonic stem cell. The method includes treating the mammalian cytoplasmic donor cell line with a DNA interchelating agent to obtain a functionally enucleated mammalian cytoplasmic donor cell line; treating the functionally enucleated mammalian cytoplasmic donor cell line with an agglutinin to obtain an agglutinin-treated functionally enucleated mammalian cytoplasmic donor cell line. Obtaining a second cell, namely, a cell from a mammalian patient; treating the second cell with a histone deacetylase inhibitor to obtain a second cell from the mammalian patient prepared for cell fusion; and, obtaining the cell line specific to the mammalian patient having a second self-propagating differentiated cell of a cell type similar to the first cell by fusing the agglutinin-treated functionally enucleated mammalian cytoplasmic donor cell line and the second cell from the mammalian patient prepared for cell fusion.

The disclosed teachings provide a human hepatocyte cell cytoplasmic donor cell line having a self-propagating hepatocyte cell of a cell-type similar to a human hepatocyte cell. The human hepatocyte cell is a cell obtained from a human fetal liver or a cell obtained from a human adult liver. A functionally enucleated human cancer cell is obtained by treating a human cancer cell with a DNA interchelating agent. The human cancer cell can be a human hepatoma cell, a human colorectal carcinoma cell, a Burkitt lymphoma cell, or, a T-cell leukemia cell. The human hepatocyte cell cytoplasmic donor cell line is obtained by fusing the human hepatocyte cell and the functionally enucleated human cancer cell. The disclosed teachings provide a functionally enucleated human hepatocyte cell cytoplasmic donor cell line obtained by treating the human hepatocyte cell cytoplasmic donor cell line with a DNA interchelating agent. The disclosed teachings provide a hepatocyte cell line specific to a human patient. The patient specific hepatocyte cell line has a self-propagating hepatocyte cell of a cell type similar to a hepatocyte cell of the human patient. The patient specific hepatocyte cell line is prepared by fusing a functionally enucleated human hepatocyte cell cytoplasmic donor cell line with a cell from the human patient. The cell from the human patient can be a keratinocyte, a dermal fibroblast cell, a peripheral blood cell, a peripheral mononuclear blood cell, or a bone marrow cell.

The disclosed teaching provide a human dopaminergic neuron cell cytoplasmic donor cell line having a self-propagating dopaminergic neuron cell of a cell-type similar to a human dopaminergic neuron cell. The human dopaminergic neuron cell is a cell obtained from a human fetal brain or a cell from a human adult brain. The disclosed teachings provide a functionally enucleated human cancer cell obtained by treating a human cancer cell with a DNA interchelating agent. The human dopaminergic neuron cell cytoplasmic donor cell line is obtained from fusing the human dopaminergic neuron cell and the functionally enucleated human cancer cell. A functionally enucleated human dopaminergic neuron cell cytoplasmic donor cell line is obtained by treating the human dopaminergic neuron cell cytoplasmic donor cell line with a DNA interchelating agent. The disclosed teachings provide a dopaminergic neuron cell line specific to a human patient having a self-propagating dopaminergic neuron cell of a cell type similar to a dopaminergic neuron cell of the human patient. The dopaminergic neuron cell line specific to the human patient is obtained by fusing the functionally enucleated human dopaminergic neuron cell cytoplasmic donor cell line with a cell from the human patient. The cell from the human patient can be a keratinocyte, a dermal fibroblast cell, a peripheral blood cell, a peripheral mononuclear blood cell, or a bone marrow cell. The human cancer cell can be a human hepatoma cell, a human colorectal carcinoma cell, a Burkitt lymphoma cell, or, a T-cell leukemia cell.

The disclosed teaching provide a human pancreatic beta cell cytoplasmic donor cell line having a self-propagating pancreatic beta cell of a cell-type similar to a human pancreatic beta cell. The human pancreatic beta cell is a cell obtained from a human fetal pancreas or from a human adult pancreas. A functionally enucleated human cancer cell being obtained by treating a human cancer cell with a DNA interchelating agent. The human pancreatic beta cell cytoplasmic donor cell line is obtained from fusing the human pancreatic beta cell and the functionally enucleated human cancer cell. The disclosed teachings provide a functionally enucleated human pancreatic beta cell cytoplasmic donor cell line obtained by treating the human pancreatic beta cell cytoplasmic donor with a DNA interchelating agent. A pancreatic beta cell line specific to a human patient is provided. The patient specific pancreatic beta cell line has a self-propagating pancreatic beta cell of a cell type similar to a pancreatic beta cell of the human patient. The pancreatic beta cell line specific to the human patient obtained by fusing the functionally enucleated human pancreatic beta cell cytoplasmic donor cell line with a cell from the human patient. The cell from the human patient can be a keratinocyte, a dermal fibroblast cell, a peripheral blood cell, a peripheral mononuclear blood cell, or a bone marrow cell. The human cancer cell can be a human hepatoma cell, a human colorectal carcinoma cell, a Burkitt lymphoma cell, or, a T-cell leukemia cell.

The disclosed teachings provide a method of preparing a hepatocytic human cell line specific to a human patient. The disclosed teachings provide a method of preparing a patient-specific dopaminergic cell line. The disclosed teachings provide a patient specific pancreatic beta cell line. The disclosed teachings provide a method of obtaining a human cancer cell, treating the human cancer cell with a DNA interchelating agent to obtain a functionally enucleated human cancer cell, treating the functionally enucleated human cancer cell with an agglutinin to obtain an agglutinin-treated functionally enucleated human cancer cell. In some embodiments, the method discloses obtaining a human hepatocyte cell from a human fetal liver or from a human adult liver. Next a human hepatocyte cytoplasmic donor cell line having a self-propagating human hepatocyte cell of a cell type similar to the human hepatocyte cell is obtained. The self-propagating human hepatocyte cell is obtained by fusing the human hepatocyte cell with the agglutinin-treated functionally enucleated human cancer cell. The self-propagating human hepatocyte cytoplasmic donor cell line is treated with a DNA interchelating agent to obtain a functionally enucleated human hepatocyte cytoplasmic donor cell line. The functionally enucleated human hepatocyte cytoplasmic donor cell line is treated with an agglutinin to obtain an agglutinin-treated functionally enucleated human hepatocyte cytoplasmic donor cell line. A cell from a human patient is treated with a histone deacetylase inhibitor to provide a cell from the human patient prepared for cell fusion. The hepatocytic cell line specific to the human patient having a self-propagating hepatocyte cell of a cell type similar to a hepatocyte cell of the human patient is obtained by fusing the agglutinin-treated functionally enucleated cytoplasmic donor cell line and the cell from the human patient prepared for cell fusion.

The disclosed teachings provide a method of preparing a dopaminergic neuron cell line specific to a human patient.

The disclosed teachings provide a method of preparing a pancreatic beta cell line specific to a human patient.

BRIEF DESCRIPTION OF THE DRAWINGS

The above objectives and advantages of the disclosed teachings will become more apparent by describing in detail preferred embodiments thereof with reference to the attached drawings in which:

FIG. 5 is a table providing fingerprinting (Short Tandem Repeat) analysis of various genetic loci from patient-specific hepatocytic cell lines, EIH-1Fb and EIH-4, and the patient cells, 4299 fibroblast and PCA1584 peripheral blood mononuclear cells (PBMNC) respectively, that were epigenetically induced by fusion with functionally enucleated HFL-140 cells.

FIG. 10 provides a table with fingerprinting (Short Tandem Repeat) analysis of various genetic loci in patient-specific pancreatic beta cell lines, EIPB-2Fb and EIPB-3 and the patient cells, 4299 and A1749, which were epigenetically induced to form the patient specific pancreatic beta cell lines.

FIG. 14 provides a table providing fingerprinting (Short Tandem Repeat) analysis of various genetic loci from the patient-specific dopaminergic neuron cell lines, EIDN-3AFb and EIDN-4, and the patient cells, 4299 fibroblast and A1748 PBMNC respectively, which were used for epigenetic induction.

DETAILED DESCRIPTION

Figure 1:
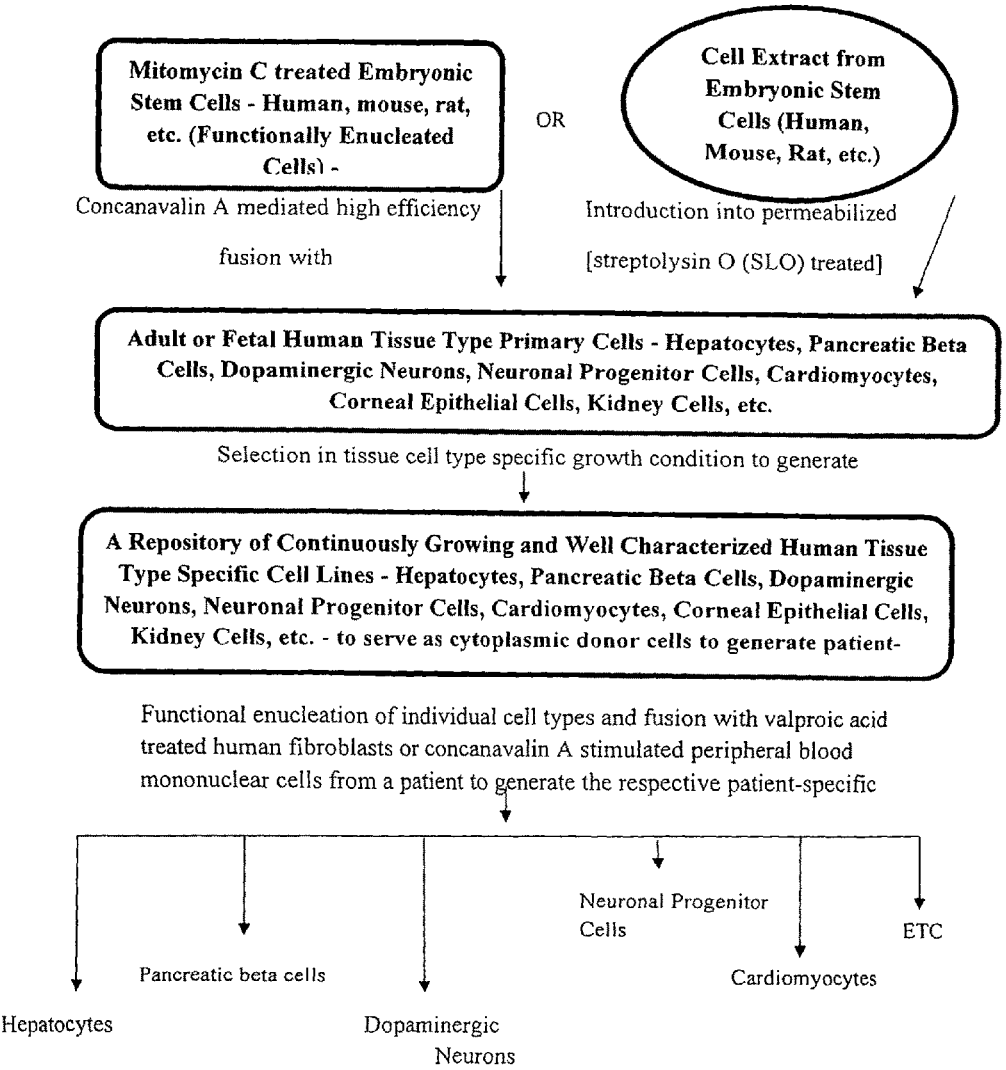
FIG. 1 provides a schematic representation of the method to develop a cell line specific to a patient. The patient-specific cell line is prepared by fusion of differentiated cells obtained from a patient with the tissue specific repositiory of cytoplasmic donor cell lines.

The disclosure provides a method for generating patient-specific differentiated cells from primary cells, such as, human fibroblasts or blood mononuclear cells by epigenetic induction. In some embodiments, a method is presented to generate pure populations of patient-specific dopaminergic neurons, liver cells, and insulin producing beta cells from primary adult human fibroblast and PBMNC by epigenetic induction. These epigenetically induced (EI) cells can also be expanded in culture. The method can be used to generate almost any differentiated cell type from human primary cells by epigenetic induction.

In some embodiments, human dopaminergic neuron, liver and pancreatic beta cytoplasmic donor cell lines are generated by fusing the respective primary cells isolated from human fetal brain, liver, and pancreas tissues with functionally enucleated mouse embryonic stem cells. In some embodiments, the human cytoplasmic donor cell lines are used as cytoplasmic donor cells to epigenetically induce adult human primary fibroblast cells and concanavalin A stimulated peripheral blood mononuclear cells (PBMNC) to generate patient-specific human dopaminergic neurons, hepatocytes, and beta cells respectively. The paradigm presented here can be used to develop almost any patient-specific cell type for various clinical applications.

In one embodiment a mammalian cytoplasmic donor cell line is provided. The mammalian cytoplasmic donor cell line includes a first self-propagating differentiated cell of a cell-type similar to a first cell. The mammalian cytoplasmic donor cell line is obtained from fusing the first cell and a functionally enucleated mammalian embryonic stem cell. The first cell is a differentiated cell from a mammalian tissue. The functionally enucleated mammalian embryonic stem cell is obtained by functionally enucleating a mammalian embryonic stem cell.

In some embodiments, the mammalian embryonic stem cell is obtained from a human. In some embodiments, the mammalian embryonic stem cell is obtained from a rat. In some embodiments, the mammalian embryonic stem cell is obtained from mouse. In some embodiments, a mouse embryonic stem cell is functionally enucleated to form a functionally enucleated mouse embryonic stem cell. In some embodiments, a functionally enucleated human embryonic stem cell is obtained by functionally enucleating a human embryonic stem cell. In some embodiments, a functionally enucleated rat embryonic stem cell is obtained by functionally enucleating a rat embryonic stem cell. In some embodiments, the mammalian tissue from which the first cell, which is the differentiated cell from the mammalian tissue, is obtained is a human adult tissue. In some embodiments, the mammalian tissue from which the first cell, which is the differentiated cell from the mammalian tissue, is obtained is a human fetal tissue. In some embodiments, the mammalian tissue from which the first cell, which is the differentiated cell from the mammalian tissue, is obtained is a human fetal liver. In some embodiments, the mammalian tissue from which the first cell, which is the differentiated cell from the mammalian tissue, is obtained is a human adult liver. In some embodiments, the mammalian tissue from which the first cell, which is the differentiated cell from the mammalian tissue, is obtained is a human fetal brain. In some embodiments, the mammalian tissue from which the first cell, which is the differentiated cell from the mammalian tissue, is obtained is a human adult brain. In some embodiments, the mammalian tissue from which the first cell, which is the differentiated cell from the mammalian tissue, is obtained is a human fetal pancreas. In some embodiments, the mammalian tissue from which the first cell, namely, the differentiated cell from the mammalian tissue, is obtained is a human adult pancreas. In some embodiments, the first cell is a dopaminergic neuron cell. In some embodiments, the first cell is a hepatic cell. A hepatic cell is also referred to as a hepatocyte cell or a hepatocytic cell. In some embodiments, the first cell is a pancreatic beta cell. In some embodiments, the first cell is a human dopaminergic neuron cell. In some embodiments, the first cell is a human hepatic cell or a hepatocyte cell. In some embodiments, the first cell is a human pancreatic beta cell. In some embodiments, the mammalian cytoplasmic donor cell line is a human hepatocyte cell cytoplasmic donor cell line. In some embodiments, the mammalian cytoplasmic donor cell line is a human dopaminergic neuron cell cytoplasmic donor cell line. In some embodiments, the mammalian cytoplasmic donor cell line is a human pancreatic beta cell cytoplasmic donor cell line.

In some embodiments, the human dopaminergic neuron cell cytoplasmic donor cell line is obtained by fusing a human dopaminergic neuron cell and a functionally enucleated mouse embryonic stem cell line. In some embodiments, the human hepatocyte cell cytoplasmic donor cell line is obtained by fusing a human hepatocytic cell and a functionally enucleated mouse embryonic stem cell line. In some embodiments, the human pancreatic beta cell cytoplasmic donor cell line is obtained by fusing a human pancreatic beta cell and a functionally enucleated mouse embryonic stem cell line.

In some embodiments, the human dopaminergic neuron cell cytoplasmic donor cell line is obtained by fusing a human dopaminergic neuron cell and a functionally enucleated human cancer cell line. In some embodiments, the human hepatocyte cell cytoplasmic donor cell line is obtained by fusing a human hepatocytic cell and a functionally enucleated human cancer cell line. In some embodiments, the human pancreatic beta cell cytoplasmic donor cell line is obtained by fusing a human pancreatic beta cell and a functionally enucleated human cancer cell line. The human cancer cell can be a human hepatoma cell, a human colorectal carcinoma cell, a Burkitt lymphoma cell, or, a T-cell leukemia cell.

In one embodiment, a functionally enucleated mammalian cytoplasmic donor cell line is provided. The functionally enucleated mammalian cytoplasmic donor cell line is obtained by functionally enucleating a mammalian cytoplasmic donor cell line. The mammalian cytoplasmic donor cell line is obtained from fusing the first cell and a functionally enucleated mammalian embryonic stem cell. In some embodiments, the mammalian cytoplasmic donor cell line is obtained from fusing the first cell and a functionally enucleated human cancer cell line. The first cell is a differentiated cell from a mammalian tissue. The functionally enucleated mammalian embryonic stem cell is obtained by functionally enucleating a mammalian embryonic stem cell. In some embodiments, the mammalian patient is human. In some embodiments, the mammalian patient is a mouse. In some embodiments, the mammalian patient is a rat.

One embodiment relates to fusing a non-embryonic cell from a patient with a functionally enucleated mammalian cytoplasmic donor cell to epigenetically induce the differentiation of a patient specific cell into the cell type of the mammalian cytoplasmic donor cell to form a differentiated patient specific cell. In another embodiment, the patient specific (epigenetically induced) cell continuously grows in a tissue culture medium.

In some embodiments, the second self-propagating differentiated cell is a hepatocyte cell. In some embodiments, the second self-propagating differentiated cell is a dopaminergic neuron cell. In some embodiments, the second self-propagating differentiated cell is a pancreatic beta cell.

In some embodiments, the cell line specific to the mammalian patient is a human hepatocyte cell line specific to a human patient. In some embodiments, the cell line specific to the mammalian patient is a human dopaminergic neuron cell line specific to a human patient. In some embodiments, the cell line specific to the mammalian patient is a human pancreatic beta cell line specific to a human patient.

In order to epigenetically reprogram adult human primary cells directly into specific differentiated cell types and also to expand them in culture to meet the demand for various applications, the following criteria have to be met:
(1) The primary cells should be easily isolatable, such as dermal fibroblasts, peripheral blood mononuclear cells (PB-MNC), keratinocytes, and bone marrow mononuclear cells;
(2) Availability of well established cell lines to serve as cytoplasmic donors for epigenetic induction of human primary cells;
(3) The cytoplasmic donor cells should also have the capacity to induce continuous growth in (patient-specific adult cells used in step 1 as) recipient cells; and,
(4) A highly efficient cell fusion method.

One of the characteristic features of embryonic stem (ES) cells is their unlimited growth potential in their undifferentiated state. It may also be possible that the ability of the ES cells for unlimited growth potential in their undifferentiated state may be cytoplasmically transferred to primary differentiated cells isolated from any tissue to obtain continuously growing differentiated cell lines. Such continuously growing differentiated cell lines can then serve as cytoplasmic donor cells to epigenetically induce adult mammalian or human primary cells to the cytoplasmic donor cell phenotype, and, with the ability to grow continuously in culture.

In one embodiment, a human dopaminergic neuron cell line that can be used as a mammalian cytoplasmic donor cell line for preparing patient-specific dopaminergic neuron cell line is provided. In one embodiment, a human hepatocyte cell line that can be used as mammalian cytoplasmic donor cell line to generate a patient-specific hepatocyte cell line is provided. In one embodiment, a human pancreatic beta cell line that can be used as a mammalian cytoplasmic donor cell line for preparing patient-specific pancreatic beta cell lines that can be used as mammalian cytoplasmic donor cell lines is provided. In some embodiments, primary cells isolated from human fetal tissues, such as, brain, liver and pancreas are fused with a functionally enucleated mouse ES cell line, such as E14TG, to form a human cytoplasmic donor cell line for preparing patient-specific dopaminergic neuron cells, for human cytoplasmic donor cell line for preparing patient-specific hepatocyte cells, and a human cytoplasmic donor cell line for preparing patient-specific pancreatic beta cells are provided. In some embodiments, ES cell lines from other species including human, rat, and mouse are used to develop tissue type specific cytoplasmic donor cell lines. In some embodiments, the cytoplasmic donor cell lines for human cytoplasmic donor cell line for human dopaminergic neuron cells, for human hepatocyte cells, and for pancreatic beta cells, bring about epigenetic induction of adult human fibroblasts and concanavalin A (Con A) stimulated PBMNC into patient-specific dopaminergic neurons, liver (hepatocyte) cells, and beta cells respectively. These epigenetically Induced (EI) cells can be grown in continuous culture for several passages. This paradigm for developing patient-specific cell lines can be applied to generate almost any cell type from adult human primary fibroblasts and Con A stimulated PBMNC by epigenetic induction.

A schematic representation of the technology used to generate patient-specific tissue cell types for clinical and drug discovery applications is given in FIG. 1. In this method, differentiated cell types from mammalian tissues are fused with functionally enucleated mammalian embryonic stem cell lines to generate cytoplasmic donor cells lines specific to the differentiated cell type isolated from the tissue. Patient-specific differentiated cells are fused with functionally enucleated cytoplasmic donor cells line to generate patient-specific differentiated cell types that are similar to the cytoplasmic donor cell line cell type. The important steps of the technology to generate patient-specific tissue cell types from adult human primary fibroblasts and Con A stimulated PBMNC by epigenetic induction are:
1. Development of methods to isolate and grow tissue specific primary cell types from adult and fetal human tissues.
2. Development of high efficiency cell fusion method of functionally enucleated ES cells with various human primary cell types.
3. Selection of continuously growing and well characterized tissue specific cell lines—hepatocytes, dopaminergic neurons, neuronal progenitor cells, pancreatic beta cells, etc.—A repository of cell lines that will serve as cytoplasmic donor cells to generate patient-specific tissue cell types.
4. Fusion of functionally enucleated cell lines from the repository with valproic acid treated adult human fibroblasts or Con A stimulated PBMNC from patients to generate respective patient-specific cell types for various applications.

In one embodiment, a cell line specific to a mammalian patient is provided. The cell line specific to the mammalian patient has a second self-propagating differentiated cell of a cell type similar to the first cell. The cell line specific to the mammalian patient is obtained from fusing a functionally enucleated mammalian cytoplasmic donor cell line and a second cell. The functionally enucleated mammalian cytoplasmic donor cell is obtained by fusing a mammalian embryonic stem cell with a first cell which is a differentiated cell from a mammalian tissue.

The second cell is a cell obtained from the mammalian patient. In some embodiments, the second cell is a keratinocyte. In some embodiments, the second cell is a dermal fibroblast cell. In some embodiments, the second cell is a peripheral blood cell. In some embodiments, the second cell is a peripheral mononuclear blood cell. In some embodiments the second cell is a bone marrow cell.

In one embodiment, a method of preparing a cell line specific to the mammalian patient is provided. The method includes obtaining a mammalian embryonic cell, treating the mammalian embryonic cell with a DNA interchelating agent to obtain a functionally enucleated mammalian embryonic cell, treating the functionally enucleated mammalian embryonic stem cell with an agglutinin to obtain an agglutinin-treated functionally enucleated mammalian embryonic stem cell.

In one embodiment, the method further includes, obtaining a first cell which is a differentiated cell from a mammalian tissue. The method further includes obtaining a mammalian cytoplasmic donor cell line having a first self-propagating differentiated cell of a cell type similar to the first cell by fusing the first cell with the agglutinin-treated functionally enucleated mammalian embryonic stem cell. The method includes, treating the mammalian cytoplasmic donor cell line with a DNA interchelating agent to obtain a functionally enucleated mammalian cytoplasmic donor cell line. The method includes treating the functionally enucleated mammalian cytoplasmic donor cell line with an agglutinin to obtain an agglutinin-treated functionally enucleated mammalian cytoplasmic donor cell line. The method includes obtaining a second cell from a mammalian patient, treating the second cell with a histone deacetylase inhibitor to obtain a second cell from the mammalian patient prepared for cell fusion, and, obtaining the cell line specific to the mammalian patient. The cell line specific to the mammalian patient includes a second self-propagating differentiated cell of a cell type similar to the first cell. The cell line specific to the mammalian patient is obtained by fusing the agglutinin-treated functionally enucleated mammalian cytoplasmic donor cell line and the second cell from the mammalian patient prepared for cell fusion. In some embodiments, patient refers to any mammal from whom differentiated cells were obtained to create epigenetically induced cell lines specific to that mammal.

FIG. 1 provides a schematic representation of the method to develop a cell line specific to a patient. Embryonic stem cells from human, mouse, rat, etc. are treated with mitomycin C to obtain functionally enucleated cells. The functionally enucleated cells are fused with adult or fetal human tissue-type primary cells, such as, hepatocytes, pancreatic beta cells, dopaminergic neurons, neuronal progenitor cells, cardiomyocytes, corneal epithelial cells, kidney cells, etc. Alternatively, cell extract prepared from embryonic stem cells obtained from mammals, such as, human, mouse or rat is introduced into permeablized adult or fetal human tissue-type primary cells. The adult or fetal human tissue-type primary cells can include cells from any tissue in the mammal. For example, adult or fetal human tissue-type primary cells can be hepatocytes, pancreatic beta cells, dopaminergic neurons, neuronal progenitor cells, cardiomyocytes, corneal epithelial cells, kidney cells, etc. The permeabilization of adult or fetal human tissue-type primary cells can be performed by methods, such as, streptolysin treatment (SLO). Following the fusion the cells can be selected by growing them in growth medium known to be suitable for growth of cells belonging to specific tissue type of the adult or fetal human tissue-type primary cells, whereby, tissue specific repository of cytoplasmic donor cells lines having a cell-type similar to the adult or fetal human tissue-type primary cells is obtained. Tissue-type specific cell line can be created for human cells, such as, hepatocytes, pancreatic beta cells, dopaminergic neurons, neuronal progenitor cells, cardiomyocytes, corneal epithelial cells, kidney cells, etc., to serve as cytoplasmic donor cells to generate patient-specific tissue cell types for clinical and other applications. FIG. 1 further shows that patient-specific cell lines are prepared from differentiated cells obtained from the patient, such as human fibroblasts cells. The human fibroblast cells can be treated with valproic acid and fused with functionally enucleated cells from the tissue specific repositiory of cytoplasmic donor cell lines to obtain patient-specific cell lines having patient specific cells of a type that are similar to the adult or fetal human tissue-type primary cell that was used to generate the cytoplasmic donor cell line. Alternatively, concanavalin A stimulated peripheral blood cells from a patient can be fused with functionally enucleated cells from the tissue specific repositiory of cytoplasmic donor cell lines to obtain patient-specific cell lines having patient specific cells of a type that are similar to the adult or fetal human tissue-type primary cell that was used to generate the cytoplasmic donor cell line. Patient specific cell lines can be obtained for cell types belonging to any tissue. Some examples include patient specific cell lines having cells, such as, hepatocytes, pancreatic beta cells, dopaminergic neurons, neuronal progenitor cells, cardiomyocytes etc.

In some embodiments, the first cell, namely, the differentiated cell from the mammalian tissue is a human hepatocyte cell, a human dopaminergic neuron cell or a human pancreatic beta cell. In some embodiments, the mammalian patient is a human, a mouse or a rat.

In some embodiments of the method of obtaining a cell line specific to a mammalian patient includes growing mammalian tissue in a dish. The dish has a tissue culture medium. A floating population of cells which has the differentiated cell from the mammalian tissue is obtained from the cells growing in the dish. The floating population of cells, which is prepared from the differentiated cell from the mammalian tissue, has the first cell.

In some embodiments, the tissue culture medium is the complete tissue culture medium, complete tissue culture medium having human EGF and human basic FGF, a tyrosine-free medium, a tyrosine-free medium having human EGF, human basic FGF and dexamethasone, and, tyrosine-free medium having human EGF and human basic FGF. The concentration of human EGF and basic FGF range from about 1 nanogram per milliliter to about 20 ng per milliliter. In some embodiments, dexamethasone ranges from about 0.01 uM to about 1 uM.

In one embodiment, a floating population of cells is prepared from a differentiated cell such as a hepatocyte from a mammalian tissue. In another embodiment, a floating population of cells is prepared from a differentiated cell, such as, a pancreatic beta cell from a mammalian tissue.

In some embodiments, a floating population of cells is prepared from the patient specific cell line. In some embodiments, the floating population of cells is the second cell line.

In some embodiments, the floating population of cells is a mammalian patient specific hepatocytic cell line.

In some embodiments of the method of preparing a patient specific cell line, the mammalian embryonic cell is a human embryonic stem cell. In some embodiments of the method of preparing a patient specific cell line, the mammalian embryonic cell is a mouse embryonic stem cell.

Methods for functionally enucleating cells are well known. In some embodiments, a DNA interchelating agent is used. In some embodiments, the DNA interchelating agent can be mitomycin C, ethidium bromide or DAPI [Gopalakrishnan, T. V. and J. W. Littlefield, RNA from rat hepatoma cells can activate phenylalanine hydroxylase gene of mouse erythroleukemia cells. Somatic Cell Genet, 1983. 9(1): p. 121-31.].

In some embodiments, an agglutin is used. In some embodiments, the agglutinin is concanavalin A, phytohemagglutinin, or wheat germ lectin.

In some embodiments, the histone deacetylase inhibitor is valproic acid, trichostatin A, or vorinostat.

In some embodiments of obtaining the patient specific cell line, the mammalian tissue is human fetal liver, human adult liver, human fetal brain, human adult brain, human fetal pancreas, or human adult pancreas.

In some embodiments provide a method of treatment by administering the second cell line, namely the patient specific cell line, to the mammalian patient. In some embodiments, the mammalian patient is a human, a mouse or a rat. The method of treatment can be applied to human or other mammalian patients suffering from a disease, such as, liver failure, cirrhosis, Alzheimer's disease, Parkinson's disease, or diabetes.

In one embodiment a tissue is created. The tissue is specific to the patient from whom cells were obtained to generate patient-specific cell lines by epigenetic induction.

Some embodiments include transplantation of patient specific cell lines into patients from whose cells were used to generate the respective patient-specific cell lines were generated by epigenetic induction.

The generated cell lines can be used for applications, such as, drug discovery and drug toxicology studies. The cell lines generated by the methods disclosed can be used for biological production for therapeutic use. In some embodiments, the mammalian cytoplasmic donor cell line or the patient specific cell line are used for drug discovery, drug development, drug toxicology studies, drug development, hepatitis research, preparation of human biological molecules, or used in clinical setting. Human biological molecules that can be prepared from the cell lines include albumin, insulin and clotting factors.

In some embodiments, human hepatocyte cell lines have been developed by fusing human adult or fetal liver primary hepatocytes with a functionally enucleated human tumor cell line. The human tumor cell lines include, human hepatoma, Hep G2 (ATCC#HB-8065); human colorectal carcinoma, T-84 (ATCC # CCL-248); Burkitt lymphoma, Daudi (ATCC# CCL-213); or T-Cell leukemia, Jurkat (ATCC# TIB-152). In some embodiments, human pancreatic beta cell lines have been developed by fusing adult or fetal pancreatic beta cells with a functionally enucleated HepG2 or a Daudi cell line. In some embodiments, human dopaminergic neuron cell lines have been developed by fusing fetal brain dopaminergic neuron cells with a functionally enucleated Daudi cell line. The cell lines resulting from the fusion can be grown continuously in culture. These experiments establish a new paradigm to develop immortalized human cell lines through epigenetic activation of continuous growth property by fusing various human primary cells with a number of human tumor cell lines.

The results showed that well established cancer cell lines are capable of transmitting the continuous growth property, a hall mark property of all cancer cell lines, to normal adult human cells purely through epigenetic mechanisms. Four different cancer cell lines were obtained from ATCC, namely, human hepatoma, Hep G2 (ATCC#HB-8065); human colorectal carcinoma, T-84 (ATCC # CCL-248); Burkitt lymphoma, Daudi (ATCC# CCL-213); and T-Cell leukemia, Jurkat (ATCC# TIB-152). The cancer cell lines were used as cytoplasmic donor cells for fusion with normal adult or fetal liver hepatocyte cells. Normal hepatocyte cells, which do not grow in culture, were transformed into continuously growing population of cells following fusion with functionally enucleated cancer cell lines. In addition, the newly transformed hepatocyte cell lines maintained all of the differentiated characteristics of normal hepatocyte cells. The cancer cell lines were also capable of immortalizing adult or fetal pancreatic beta cells through epigenetic activation. The immortalized pancreatic beta cell lines also maintained the ability to produce insulin similar to normal pancreatic beta cells. Fetal brain dopaminergic neuron cells have also been immortalized following fusion with functionally enucleated cancer cell lines. The immortalized dopaminergic neuron cell lines maintained the characteristic property of dopaminergic neuron cells. These experiments show that many cancer cell lines can be used to develop immortalized human cell lines of various differentiated cell types by fusing them with functionally enucleated human cancer cell lines. This general paradigm of epigenetic activation of growth can be used for immortalization of any normal human cells. The immortalized human cell lines can be further used in the preparation of patient-specific cell lines.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

EXAMPLES

Example 1

Epigenetically-Induced Hepatocyte (EIH) Cells

Human hepatocyte cell lines were developed by cytoplasmic activation of continuous growth in primary hepatocytes through fusion of the primary hepatocytes with a functionally enucleated mouse ES cell line, namely, E14Tg2a (ATCC; [Kuehn, M. R., et al., A potential animal model for Lesch-Nyhan syndrome through introduction of HPRT mutations into mice. Nature, 1987. 326(6110): p. 295-8.]).

The functionally enucleated mouse ES cells did not give rise to any cells that were morphologically similar to the ES cells following fusion of the ES cells with a wide variety of differentiated human cells, such as human fibroblasts, human neuronal progenitor cells, human dopaminergic neuronal cells, human pancreatic beta cells, human astrocytes etc.

However, the fusion of the functionally enucleated mouse embryonic cells with the differentiated human cells yielded permanent cell lines having the cell phenotype of the parental differentiated human cell, and, moreover, the cell lines could be grown continuously in culture. These cell lines having differentiated human cells were used as human cytoplasmic donors for creating patient specific differentiated cells of the same cell type as the human cytoplasmic donor cell.

A cell bank of different cell types was created to serve as cytoplasmic donor to generate these cell types from adult human primary cells by epigenetic induction. Identification of the right growth condition for selecting the cell lines was very important for the success of these experiments.

Figure 2:
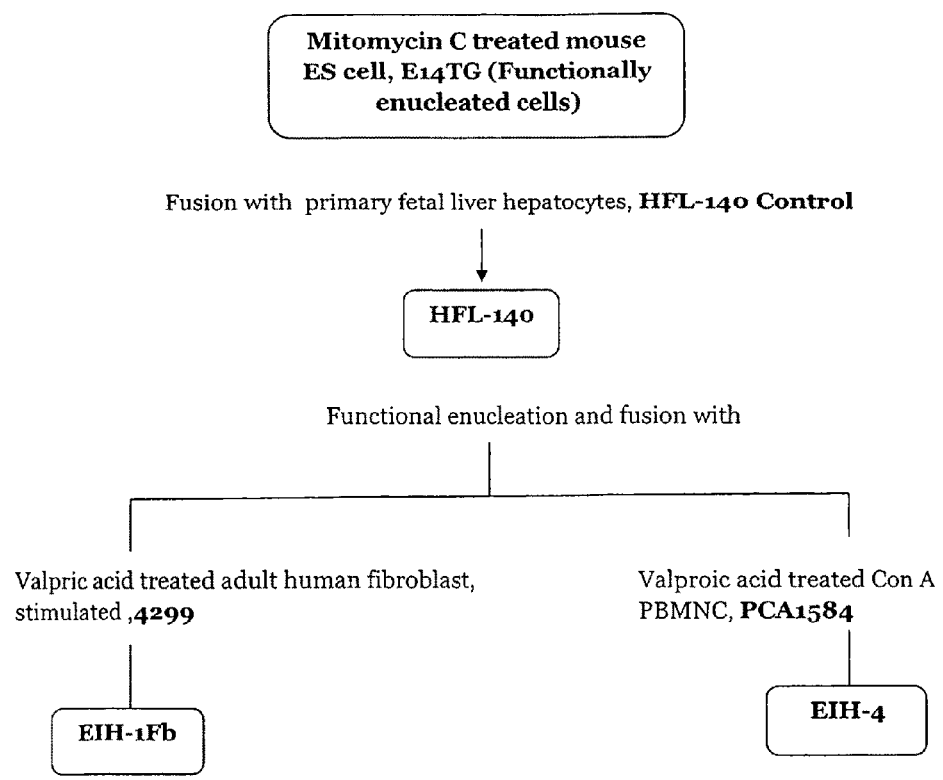
FIG. 2 is a schematic representation of development of a hepatocytic cytoplasmic donor cell line, and development of a patient-specific hepatocytic cell line by epigenetic induction.

FIG. 2 shows that the hepatocyte cell line, HFL-140 control, which has primary fetal liver hepatocytes, was used to generate a cytoplasmic donor cell line by fusing the HFL-140 control cells with mitomycin C treated mouse ES cell line, E14TG. Following the fusion, the primary fetal liver hepatocytes, grew continuously in culture and were named the cell line as HFL-140. The HFL-140 cell line was used as a cytoplasmic donor to generate epigenetically induced hepatocyte (EIH) cells from either Con A stimulated adult human peripheral blood mononuclear cells (PBMNC) or adult human primary fibroblasts obtained from patients to form patient-specific adult human hepatocyte cell lines. The HFL-140 cell line was functionally enucleated and fused with valproic acid treated and Con A stimulated adult human PBMNC, PCA1584 to obtain the EIH-4 cell line. Alternatively, the HFL-140 cell line was functionally enucleated and fused with valproic acid treated adult human fibroblast, 4299, to obtain the EIH-1Fb cell line.

Figure 3:
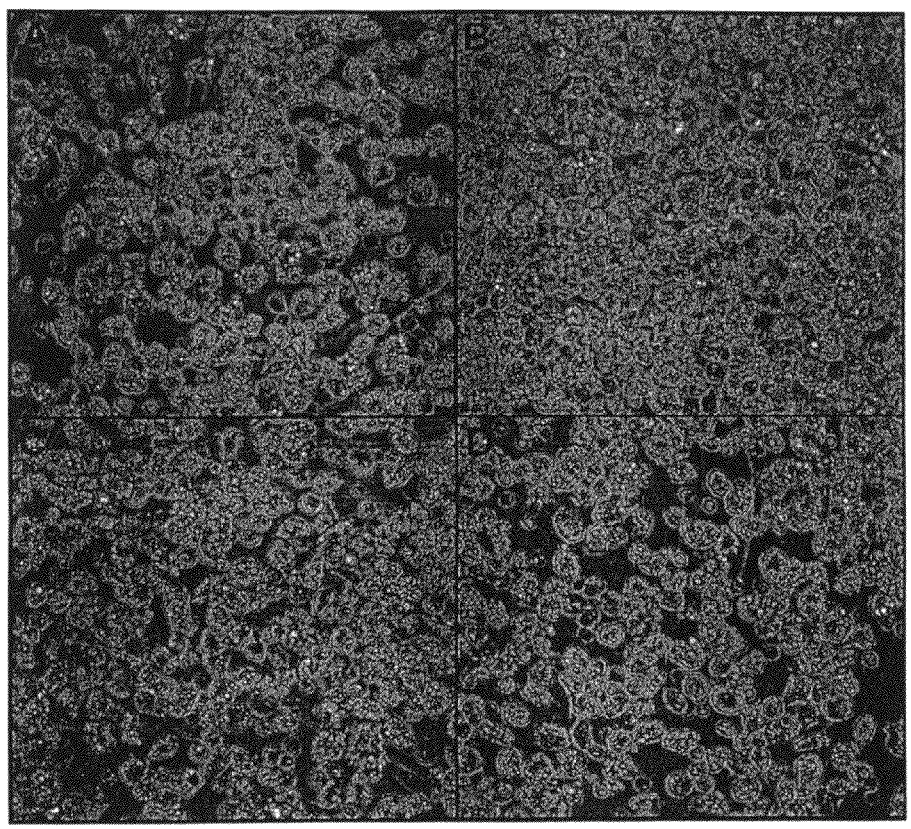
FIG. 3 provides live cell images of the fetal liver primary hepatocytic cells, HFL-140 Control (Panel A), hepatocytic cytoplasmic donor cell line, HFL-140 (Panel B), and different patient-specific epigenetically induced hepatocytic cell lines, EIH-1Fb (Panel C) and EIH-4 (Panel D).

The EIH cells from FIG. 2 grew always in suspension and did not attach to either tissue culture dishes or extracellular matrix coated dishes (see FIG. 3). FIG. 3 provides live cell images of the fetal liver primary hepatocytic cells, HFL-140 Control (panel A), hepatocytic cytoplasmic donor cell line, HFL-140 (panel B), and different patient-specific epigenetically induced hepatocytic cell lines, EIH-1Fb (panel C) and EIH-4 (panel D). FIG. 3 shows that the patient-specific hepatocytic cell lines (EIH-1Fb and EIH-4) obtained by epigenetic induction, were morphologically indistinguishable from the fetal liver primary hepatocytic cells (panel A) and the hepatocytic cytoplasmic donor cell line (panel B).

Figure 4:
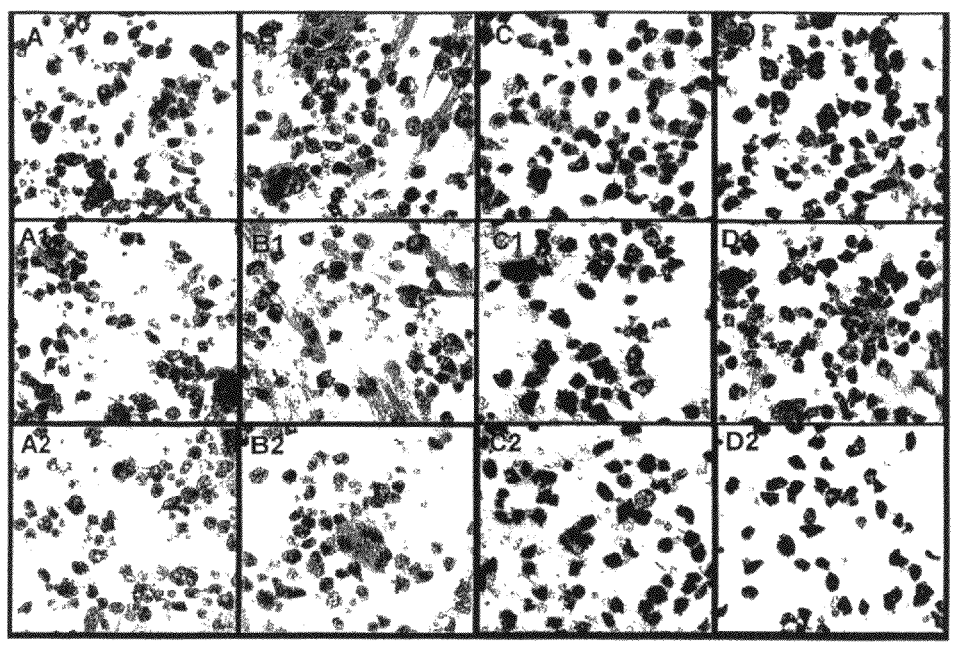
FIG. 4 provides characterization of hepatocytic cytoplasmic donor cell line, HFL-140 (Top row), and patient-specific epigenetically induced hepatocytic cell lines, EIH-1Fb (middle row) and EIH-4 (bottom row), by analysis of expression of hepatocytic cell specific functions by immunostaining. The cells show hepatocytic cell specific expression of phenylalanine hydroxylase (Panel A, A1, and A2), alpha 1-antitrypsin (Panel B, B1, and B2), albumin (Panel C, C1, and C2), and CYP3A4 (Panel D, D1, and D2).

FIG. 4 provides characterization of hepatocytic cytoplasmic donor cell line, HFL-140, and patient-specific epigenetically induced hepatocytic cell lines, EIH-1Fb and EIH-4, by analysis of expression of hepatocytic cell specific functions by immunostaining. In FIG. 4, results for HFL-140 are provided in the top row; EIH-1Fb is in the middle row, and EIH-4 is shown in the bottom row. The cells were stained for: Phenylalanine hydroxylase (panels A, A1, and A2), alpha-1 antitrypsin (panels B, B1, and B2), albumin (panels C, C1, and C2), and CYP3A4 (panels D, D1, and D2) as described in Methods section. The cells stained very strongly for all these four functions. Vector NOVA RED was used as peroxidase substrate. Peptide C (beta cell marker), and Nurr1 (dopaminergic neuron marker) were used as negative controls. The cells did not stain for these functions (data not shown). All the cells showed hepatocytic cell specific expression of phenylalanine hydroxylase, alpha 1-antitrypsin, albumin, and CYP3A4. Therefore, FIG. 4 shows that the EIH cell lines were functionally equivalent to the cytoplasmic donor hepatocyte cell line, HFL-140.

The Con A stimulated PBMNC were also treated with histone deacetylase (HDAC) inhibitor, valproic acid, as other studies have shown that valproic acid treatment improved the efficiency of nuclear reprogramming while generating iPS cells [Huangfu, D., et al., Induction of pluripotent stem cells from primary human fibroblasts with only Oct4 and Sox2. Nat Biotechnol, 2008. 26(11): p. 1269-75.]. Actively growing population of cells, EIH-4, was generated within 4-5 weeks after fusion of histone deacetylase-treated Con A stimulated PBMNC with functionally enucleated human cytoplasmic hepatocyte cytoplasmic donor cell line, HFL-140, and the cells resulting from the fusion resembled the cytoplasmic donor hepatocyte cell lines (see, FIGS. 3 and 4). The cells resulting from the fusion, EIH-4, also grew as a floating population of cells on regular tissue culture dishes (Panel D, FIG. 3) in tissue culture medium in tyrosine free medium supplemented with human EGF, human basic FGF, and expressed several hepatocyte specific functions, such as, phenylalanine hydroxylase, alpha 1 antitrypsin, albumin, and CYP3A4 (Panel A2, B2, C2, and D2, FIG. 4).

Valproic acid treated adult human fibroblasts, 4299, also gave rise to EIH cell line (EIH-1Fb) when fused with functionally enucleated hepatocyte cell line, HFL-140. This cell line was also morphologically and functionally indistinguishable from the cytoplasmic donor hepatocyte cell line, HFL-140, and primary hepatocytes (FIGS. 3 and 4). EIH cells obtained from fusion of adult human fibroblasts and the functionally enucleated hepatocyte cell line, HFL-140, appeared somewhat earlier compared to that from PBMNC. The genotype of the EIH cell lines, EIH-1Fb and EIH-4, and the respective adult human cells, 4299 and PCA1584 fused to generate the resulting cell lines, EIH-1Fb, and EIH-4, are given in the table in FIG. 5.

FIG. 5 is a table providing fingerprinting (Short Tandem Repeat) analysis of the patient-specific hepatocytic cell lines, EIH-1Fb and EIH-4, 4299 fibroblast and PCA1584 peripheral blood mononuclear cells (PBMNC) respectively. The following genetic loci were tested by STR analysis for fingerprinting the cell lines to determine their identity: Amelogenin, vWA, D8S1179, TPOX, FGA, D3S1358, THO1, D21S11, D16S51, penta E, D5S818, D13S317, D7S820, D16S539, CSF1PO, and penta D.

FIG. 5 shows that the genotypes of EIH-1Fb and EIH-4 cell lines were quite different from the genotype of the cytoplasmic donor hepatocytic cell line, HFL-140. On the other hand, FIG. 5 shows that the genotype of the EIH cell lines, EIH-1Fb and EIH-4, matched with those of the respective adult human cells, 4299 and PCA1584 that were obtained from the patient for fusion with functionally enucleated cytoplasmic donor hepatocytic cell line, HFL-140. These results confirmed that the EIH cell lines, EIH-1Fb and EIH-4, were generated by epigenetic induction and had not arisen from a rare revertant of the functionally enucleated cytoplasmic donor hepatocyte cell line, HFL-140.

Several control experiments have been carried out. No growing population of cells were ever obtained directly from valproic acid treated human fibroblasts and Con A stimulated PBMNC without fusion with the functionally enucleated hepatocyte cell lines.

No growing cell was ever seen with the hepatocytic cytoplasmic donor cell line, HFL-140, after the HFL-140 cell line was treated with a high concentration of mitomycin C to obtain functionally enucleated cytoplasmic donor HFL-140 for the various fusions. These results clearly indicate that the technology described in this application can be used to generate patient-specific hepatocyte cells through epigenetic induction of adult human primary cells.

Example 2

Epigenetically-Induced Pancreatic Beta (EIPB) Cells

Figure 6:
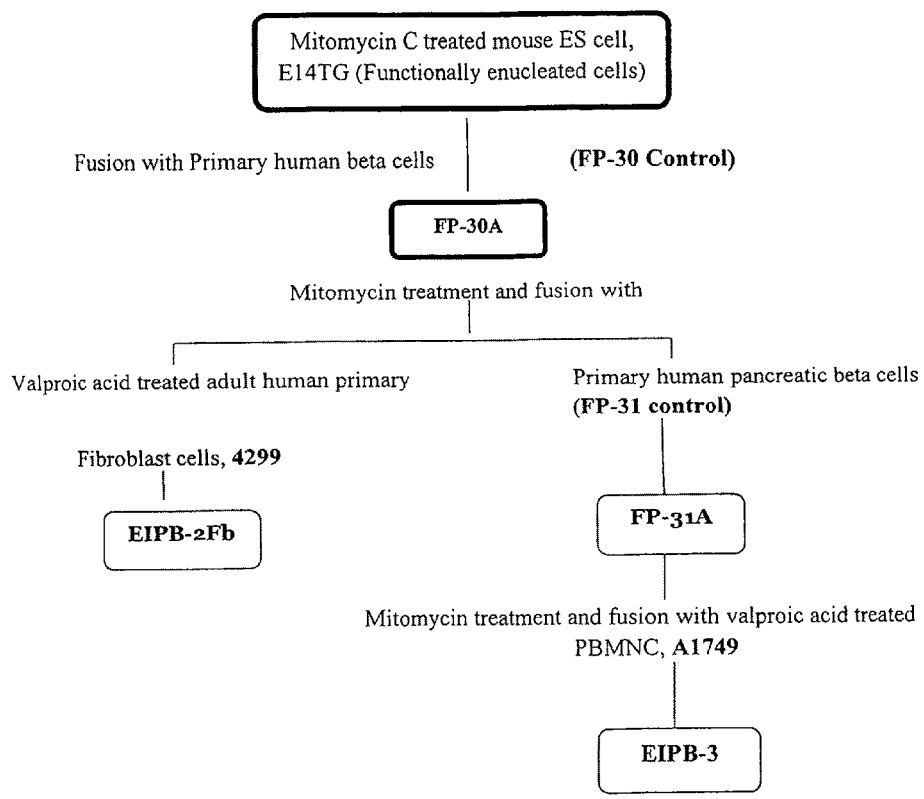
FIG. 6 provides a schematic representation of development of pancreatic beta cytoplasmic donor cell lines, FP-30A and FP-31A, and development of patient-specific pancreatic beta cell lines, EIPB-2Fb and EIPB-3 by epigenetic induction of differentiated cells, 4299 fibroblast and A1749 PBMNC respectively from the patient.

FIG. 6 shows that human cytoplasmic donor for pancreatic beta cell lines, e.g. FP-30A, were developed by cytoplasmic activation of continuous growth in primary human pancreatic beta cells, namely FP-30 (referred to as FP-30 Control in FIG.

6) through fusion with a functionally enucleated mouse ES cell line, E14Tg2a (obtained from ATCC; see, Kuehn, M. R., et al., A potential animal model for Lesch-Nyhan syndrome through introduction of HPRT mutations into mice. Nature, 1987. 326(6110): p. 295-8). The mouse embryonic stem cell line E14Tg2a was functionally enucleated by treatment with mitomycin C. The primary human pancreatic beta cells, FP-30 Control, were obtained from human fetal pancreas tissue.

The human cytoplasmic donor pancreatic beta cell line, FP-30A (FIG. 6), was used to generate another independent pancreatic beta cell line, FP-31A, by fusing functionally enucleated FP-30A cells with primary beta cells from another donor (FP-31 Control, which was isolated from another independent human fetal pancreatic tissue).

Pancreatic beta cell lines (FP-30A and FP-31A) were used as cytoplasmic donor cells to generate patient-specific epigenetically induced pancreatic beta cell (EIPB) cell lines from adult human fibroblast, and Con A stimulated adult PBMNC (FIG. 6). The adult human fibroblast, and Con A stimulated adult PBMNC were obtained from a patient.

Figure 7:
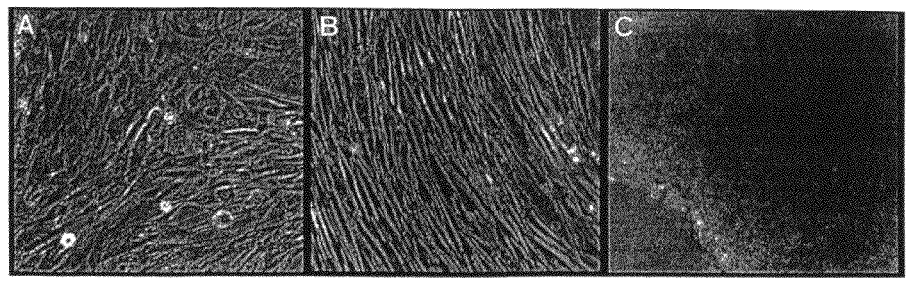
FIG. 7 provides live cell images of human cytoplasmic donor pancreatic beta cell line, FP-31A (Panel A) and epigenetically induced patient-specific beta cell lines, EIPB-2Fb (Panel B) and EIPB-3 (Panel C).

FIG. 7 provides live cell images of human cytoplasmic donor pancreatic beta cell line, FP-31A (panel A), and epigenetically induced patient-specific beta cell lines, EIPB-2Fb and EIPB-3 (Panel B and C in FIG. 7). Patient specific pancreatic beta cell line, EIPB-2Fb, resembled the human cytoplasmic donor pancreatic beta cell line, FP-31A. Patient-specific pancreatic beta cell line, EIPB-3, grew as a suspension culture (Panel C in FIG. 7).

The EIPB cell line, namely EIPB-2Fb, derived from human fibroblasts, 4299, somewhat resembled the pancreatic beta cell lines while the EIPB cell line, EIPB-3, derived from Con A stimulated adult human PBMNC, A1749, grew only in suspension (see FIG. 7).

Figure 8:
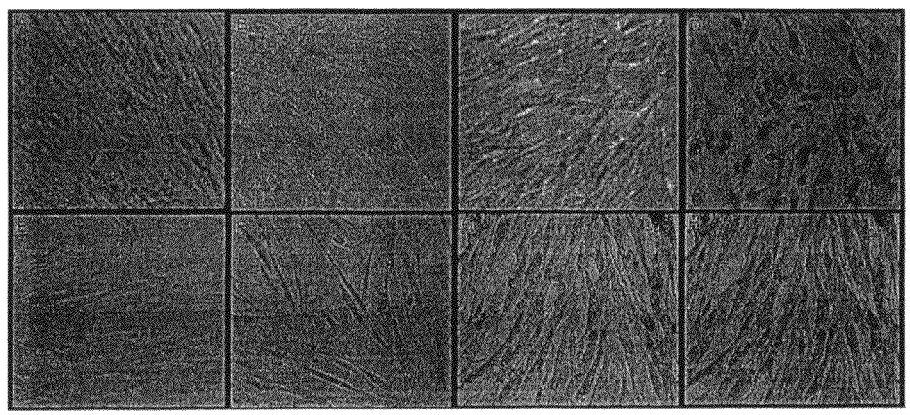
FIG. 8 provides characterization of cytoplasmic donor pancreatic beta cell line, FP-31A (Top row, panels A, B, C and D), and patient-specific epigenetically induced pancreatic beta cell lines, EIPB-2Fb (Bottom row, panels E, F, G and H), for the expression pancreatic beta cell specific functions by immunostaining. The cells were tested for expression of insulin (panels A and E), peptide C (panels B and F), PDX-1 (panels C and G), and Glut-2 (panels D and H).

However, both types of EIPB cell lines expressed several beta cell specific functions, such as, insulin, peptide C, PDX-1, and Glut-2, as tested by immunostaining (FIG. 8). FIG. 8 provides characterization of the cytoplasmic donor pancreatic beta cell line, FP-31A, and patient-specific epigenetically induced pancreatic beta cell line, EIPB-2Fb, for the expression beta cell specific functions by immunostaining. Immunostaining of FP-31A is provided in the top row (panels A, B, C and D). Immunostaining of EIPB-2Fb is provided in the bottom row (panels E, F, G and H). The cells were immunostained for expression of Insulin (see A and E); Peptide C (see B and F); PDX-1 (see C and G), and Glut-2 (see D and H). The cells were grown on tissue culture plates for staining. The staining pattern was similar in the other beta cell line (FP-30A) and EIPB cell line (EIPB-3). Albumin (hepatocyte marker) and Nurr1 (dopaminergic neuron marker) were used as negative controls, and the cells did not stain for these markers. The patient-specific epigenetically induced pancreatic beta cell line, EIPB-2FB, showed pancreatic cell specific expression of insulin, peptide C, PDX-1, and Glut-2, similar to that seen in the cytoplasmic donor pancreatic beta cell line, FP-31A.

Staining for insulin was much stronger when the cells were first grown as a cluster for one day, followed by dispersion of the clusters, and then attached to a dish. The clusters also stained strongly for dithiazone [Shiroi, A., et al., Identification of insulin-producing cells derived from embryonic stem cells by zinc-chelating dithiazone. Stem Cells, 2002. 20(4): p. 284-92.] (FIG. 9), which is an indicator of insulin production by these cells. Only cells that produce insulin stain strongly with dithiazone.

Figure 9:
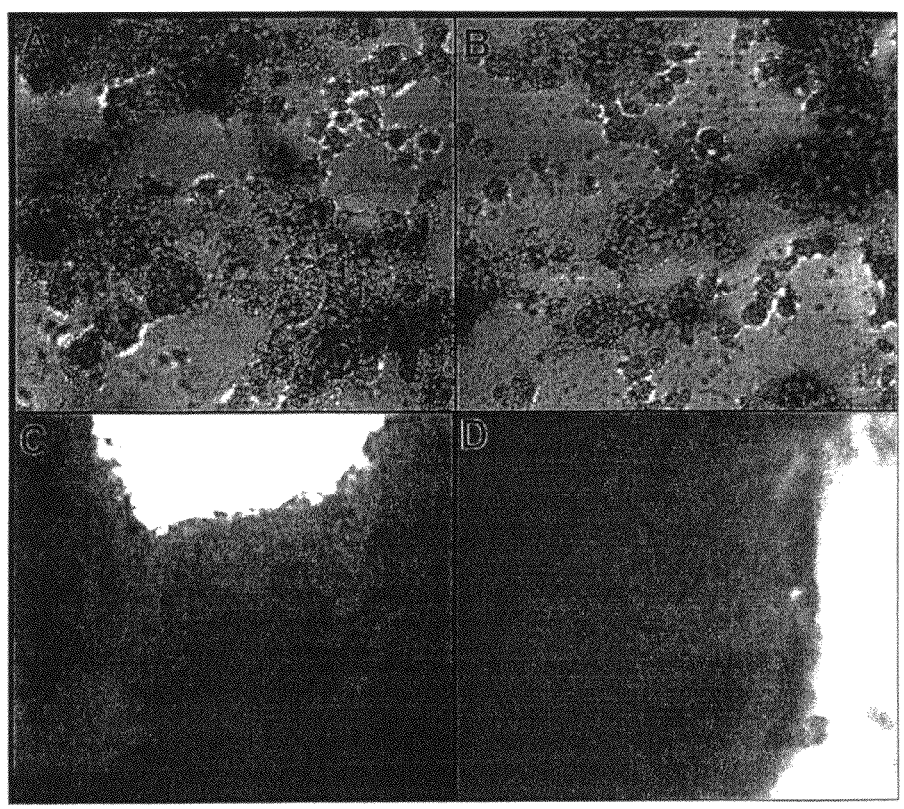
FIG. 9 provides characterization of cytoplasmic donor pancreatic beta cell line, FP-31A (Top row, panels A and B), and patient-specific pancreatic beta cell line, EIPB-2Fb (Bottom row, panels C and D) for the expression of insulin by immunostaining and diathiazone staining. The patient-specific pancreatic beta cell line was prepared by epigenetic induction of differentiated fibroblast 4299 cell from patient. The cells were grown as clusters before staining for insulin by immunostaining (Panel A and C) and dithiazone staining (Panel B and D).

FIG. 9 provides characterization of cytoplasmic donor pancreatic beta cell line, FP-31A, and patient-specific pancreatic beta cell line, EIPB-2Fb for the expression of insulin by immunostaining and diathiazone staining. FP-31A (panels A and C) and EIPB-2Fb (panels B and D) were grown as clusters for one day. The clusters were dispersed and plated on regular tissue culture plates and immunostained for Insulin (Top Row, panels A and B). The clusters are also stained directly with dithiazone to detect the presence of Insulin (Bottom Row, panels C and D). Both cell lines stained strongly for insulin and for dithiazone showing that the cells produced insulin.

The Con A stimulated PBMNC, A1749, were treated with histone deacetylase (HDAC) inhibitor, valproic acid, as it has been shown that valproic acid treatment improved the efficiency of nuclear reprogramming while generating iPS cells [Huangfu, D., et al., Induction of pluripotent stem cells from primary human fibroblasts with only Oct4 and Sox2. Nat Biotechnol, 2008. 26(11): p. 1269-75.].

Actively growing population of cells were generated after 4-5 weeks after fusion, and the EIPB cells, EIPB-3, grew only in suspension, unlike the EIPB cells, EIPB-2Fb, generated from valproic acid treated human fibroblasts (FIG. 7). Also, the EIPB cells from human fibroblast cells appeared much sooner compared to those from Con A stimulated PBMNC.

The EIPB cells from both types of adult human cells expressed several beta cell specific functions, such as, insulin, peptide C, PDX-1, and Glut-2, (see FIG. 8). The genotype of the EIPB cell lines, EIPB-1FB and EIPB-3, and the respective adult human cells, 4299 and A1749, used to generate these cell lines are given in FIG. 10.

FIG. 10 provides a table with fingerprinting (Short Tandem Repeat) analysis of the patient-specific pancreatic beta cell lines, EIPB-2Fb and EIPB-3, and the patient cells, 4299 and A1749 respectively, that were epigenetically induced to form the patient specific pancreatic beta cell lines. The following genetic loci were tested by STR analysis for fingerprinting the cell lines to determine their identity: Amelogenin, vWA, D8S1179, TPOX, FGA, D3S1358, THO1, D21S11, D16S51, penta E, D5S818, D13S317, D7S820, D16S539, CSF1PO, and penta D.

FIG. 10 shows that the genotype of the EIPB cell lines matched for all sixteen markers with those of the respective adult human cells that were used to generate them, and were quite distinct from the cytoplasmic donor beta cell lines used to generate them. FIG. 10 shows that the genotypes of the patient-specific pancreatic beta cell lines, EIPB-2Fb and EIPB-3, were quite distinct from the genotypes of the cytoplasmic donor pancreatic beta cell lines, FP-30A and FP-31A.

These results confirm that the EIPB cell lines were generated by epigenetic induction, and had not arisen from a rare revertant of the functionally enucleated cytoplasmic donor beta cell lines.

Example 3

Epigenetically Induced Dopaminergic Neuron (EIDN) Cells

Human dopaminergic (DA) neuron cell line, DAN-47A, was developed by cytoplasmic activation of continuous growth in primary DA neuron cells through fusion with functionally enucleated mouse ES cell line, E14Tg2a (ATCC; [Kuehn, M. R., et al., A potential animal model for Lesch-Nyhan syndrome through introduction of HPRT mutations into mice. Nature, 1987. 326(6110): p. 295-8.]). Other DA neuron cell lines have been developed that are not described in this application. All the DA neuron cell lines have been grown continuously in tyrosine free medium [Breakefield, X. O. and M. W. Nirenberg, Selection for neuroblastoma cells that synthesize certain transmitters. Proc Natl Acad Sci USA, 1974. 71(6): p. 2530-3.], which is a selection system used to select cells that express tyrosine hydroxylase (TH) enzyme.

Figure 11:
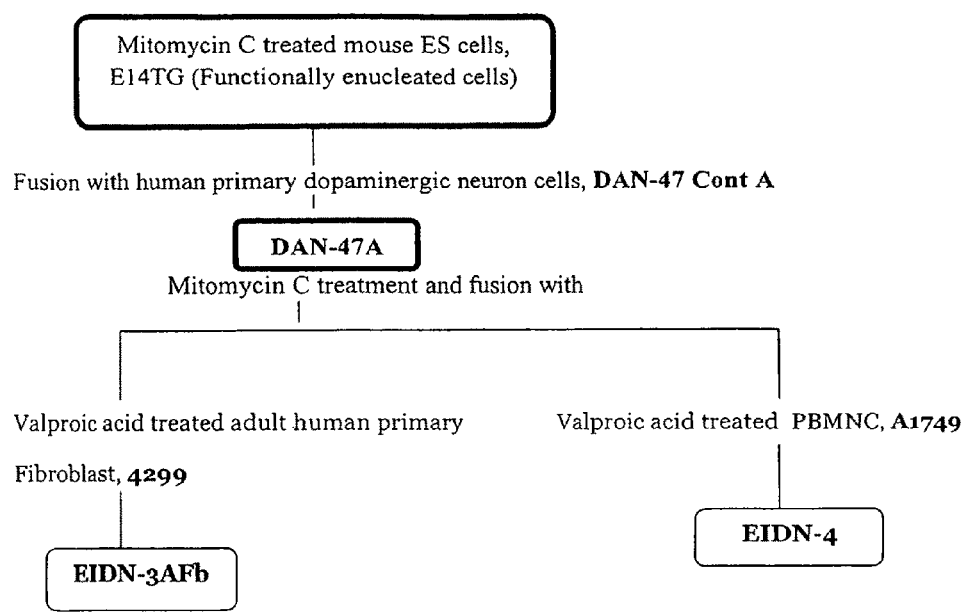
FIG. 11 provides a schematic representation of development of a cytoplasmic donor dopaminergic neuron cell line, DAN-47A, and development of patient-specific dopaminergic neuron cell lines, EIDN-3AFb and EIDN-4, by epigenetic induction.

DA neuron cell line, DAN-47A, was used as cytoplasmic donor cells to generate EIDN cell lines, EIDN-3AFb and EIDN-4, from adult human fibroblast, 4299, and Con A stimulated adult PBMNC, A1749 (FIG. 11).

FIG. 11 provides a schematic representation of development of cytoplasmic donor dopaminergic neuron cell line, DAN-47A, and development of patient-specific dopaminergic neuron cell lines, EIDN-3AFb and EIDN-4, by epigenetic induction. Cytoplasmic donor dopaminergic neuron cell line, DAN-47A, was prepared by fusing primary dopaminergic neuron cells isolated from human fetal brain tissue to functionally enucleated mouse embryonic stem cells. Patient-specific dopaminergic neuron cell lines, EIDN-3AFb and EIDN-4, were prepared by fusing valproic acid treated fibroblasts, 4299, and peripheral blood mononuclear cells, A1749, respectively to functionally enucleated cytoplasmic donor dopaminergic neuron cell line, DAN-47A. Fibroblast 4299 and PBMNC A1749 were obtained from a patient.

Figure 12:
FIG. 12 provides live cell images of cytoplasmic donor dopaminergic neuron cell line DAN-47A (Panel A), and epigenetically induced patient-specific dopaminergic neuron cell lines, EIDN-3AFb (Panel B) and EIDN-4 (Panel C).

FIG. 12 provides live cell images of cytoplasmic donor dopaminergic neuron cell line DAN-47A, and epigenetically induced patient-specific dopaminergic neuron cell lines, EIDN-3AFb and EIDN-4. Live cell images of DAN-47A are shown in panel A, EIDN-3Fb (in panel B), and EIDN-4 (in panel C). EIDN-3Fb and EIDN-4 did not form branched and long extensive processes that were seen in DAN-47A.

Figure 13:
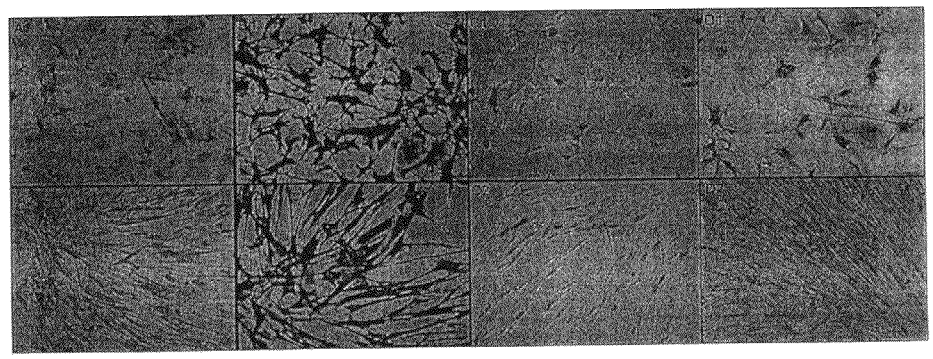
FIG. 13 provides characterization of cytoplasmic donor dopaminergic neuron cell line, DAN-47A (Top row, panels A1, B1, C1 and D1), and patient-specific epigenetically induced dopaminergic neuron cell line, EIDN-3AFb (Bottom row, panels A2, B2, C2 and D2), for the expression of dopaminergic neuron specific functions by immunostaining. Dopaminergic neuron specific functions tested were: tyrosine hydroxylase (A1 and A2), beta tubulin III (B1 and B2), Nurr1 (C1 and C2) and Pitx-3 (D1 and C2).

FIG. 13 provides characterization of cytoplasmic donor dopaminergic neuron cell line, DAN-47A, and patient-specific epigenetically induced dopaminergic neuron cell line, EIDN-3AFb, for the expression dopaminergic neuron specific functions by immunostaining. Immunostaining for dopaminergic neuron markers is shown for DAN-47A (in the Top Row, panels A1, B1, C1 and D1) and for EIDN-3Fb (in the Bottom Row, panels A2, B2, C2 and D2). The cells were stained for tyrosine hydroxylase (A1 and A2), beta tubulin III (B1 and B2), Nurr1 (C1 and C2), and Pitx-3 (D1 and D2). Uniform staining was observed for all four markers. Beta tubulin III staining was very intense compared to the other three markers. Albumin (hepatocyte marker) and peptide C (beta cell marker) were used as negative standards, and the cells did not show any staining for these two markers. EIDN-3AFb showed dopaminergic neuron specific functions, namely, tyrosine hydroxylase, beta tubulin III, Nurr1, and Pitx-3, similar to the cytoplasmic donor dopaminergic donor dopaminergic neuron cell line.

The EIDN cell lines were morphologically different from DAN-47A (FIG. 12), and expressed several DA neuron specific functions, such as, tyrosine hydroxylase, beta tubulin III, Nurr1, and Pitx-3 as tested by immunostaining (FIG. 13).

The Con A stimulated PBMNC, A1749, were treated with histone deacetylase (HDAC) inhibitor, valproic acid, as it has been shown that valproic acid treatment improved the efficiency of nuclear reprogramming while generating iPS cells [Huangfu, D., et al., Induction of pluripotent stem cells from primary human fibroblasts with only Oct4 and Sox2. Nat Biotechnol, 2008. 26(11): p. 1269-75.]. A growing population of cells was generated after 5-6 weeks after fusion, and a resulting EIDN cell line (EIDN-4) that was morphologically different from the cytoplasmic donor DA cell line, DAN-47A, was obtained (FIG. 12).

The EIDN cell line, EIDN-3AFb, generated from valproic acid treated human fibroblasts, 4299, did not form extensive processes (FIG. 12). Also, the EIDN cells from human fibroblast cells appeared much sooner and with a higher frequency compared to those from Con A stimulated PBMNC. The EIDN cells from both types of adult human cells expressed several DA neuron specific functions, such as, tyrosine hydroxylase, beta tubulin III, Nurr1, and Pitx-3 (FIG. 13).

The genotype of the EIDN cell lines, EIDN-3AFb and EIDN-4, and the respective adult human cells, 4299 and A1749, used to generate the EIDN cell lines, EIDN-3AFb and EIDN-4, are given in FIG. 14.

FIG. 14 is a table providing fingerprinting (Short Tandem Repeat) analysis of the patient-specific dopaminergic neuron cell lines, EIDN-3AFb and EIDN-4, and the patient cells, 4299 fibroblast and A1749 PBMNC respectively, which were used for epigenetic induction. The following genetic loci were tested by STR analysis for fingerprinting the cell lines to determine their identity: Amelogenin, vWA, D8S1179, TPOX, FGA, D3S1358, THO1, D21S11, D16S51, penta E, D5S818, D13S317, D7S820, D16S539, CSF1PO, and penta D.

The genotype of the EIDN cell lines, EIDN-3AFb and EIDN-4, matched with those of the respective adult human cells, 4299 and A1749, which were used to generate them. The genotypes of EIDN-3AFb and EIDN-4 are quite distinct from the genotype of the cytoplasmic donor dopaminergic neuron cell line, DAN-47A. These results confirmed that the EIDN cell lines had been generated by epigenetic induction, and had not arisen from a rare revertant of the functionally enucleated cytoplasmic donor cell line.

Example 4

Mouse Embryonic Stem Cells

Mouse embryonic stem (ES) cell line E14TG [Kuehn, M. R., et al., A potential animal model for Lesch-Nyhan syndrome through introduction of HPRT mutations into mice. Nature, 1987. 326(6110): p. 295-8.] was obtained from ATCC. The cells were grown on gelatin coated dishes in 50/50 DMEM (Dulbecco's Modified Essential Medium)/F12 (Mediatech, Inc., Manassas, Va. 20109) supplemented with 15% fetal bovine serum (FBS), 0.1 uM mercaptoethanol, non-essential aminoacids (NEAA), 1000 units/ml of LIF (Leukemia Inhibitory Factor) (Chemicon (Millipore) Billerica, Mass. 01821), gentamicin and fungizone (ES growth medium).

Example 5

Human peripheral blood mononuclear cells (PBMNC) were obtained from Stem Cell Technologies. Blood mononuclear cells were plated on poly 2-Hydroxyethyl Methacrylate (HEMA) [obtained from Sigma-Aldrich (St. Louis, Mo. 63103; Cat No: P-3932-10G]. {HEMA plates were prepared by coating the culture plates with a 5% solution of poly HEMA in 95% ethanol. Excess poly HEMA solution was removed immediately and the plates were air dried in a biological cabinet and were stored at room temperature for several weeks} plates in DF5 medium (50/50 DMEM/F12 supplemented with 5% FBS and antibiotics) supplemented with 5 ng/ml of IL-2 (Interleukin-2 obtained from PeproTech, Rocky Hill, N.J., 08553), 5 ug/ml of concanavalin A (Sigma-Aldrich, St. Louis, Mo. 63103), and 2 mM valproic acid for 24-48 hours and used for fusion with functionally enucleated human hepatocyte cell lines.

Adult human fibroblasts, 4299, was obtained from Clonetics (current name of manufacturer is Lonza, Walkersville, Md., 21793). The cells were grown on tissue culture dishes in DF5 medium. The cells were treated with 2 mM valproic acid for four days and used for fusion with functionally enucleated hepatocyte cell line.

Example 6

Functional Enucleation of Cells

Functional enucleation of ES cells was carried out using modifications of a previously published method [Gopalakrishnan, T. V. and J. W. Littlefield, RNA from rat hepatoma cells can activate phenylalanine hydroxylase gene of mouse erythroleukemia cells. Somatic Cell Genet, 9(1): p. 121-31(1983), referred to as "Gopalakrishnan et al"]. Gopalakrishnan et al showed that treatment of cells with a high concentration of Mitomycin C completely prevented contribution of single selectable gene marker necessary for the survival of hybrids following fusion with a partner cell deficient in the same selectable marker gene. Mitomycin C treatment had brought about activation of nucleases that caused the destruction of nuclear DNA.

Different cell types, mouse ES cells, HFL-140, FP-30A, FP-31A, and DAN-47A, were treated with 100 ug/ml of mitomycinC (Sigma Aldrich, St. Louis, Mo.) for three hours in suspension. The cells were collected by centrifugation and rinsed three times with HBSS, and used immediately for fusion.

Example 7

Human Hepatocyte Cell Line

Hepatocyte cells were isolated from fetal liver tissue obtained from Advanced Biosciences Resources, Inc. (Alameda, Calif. 94501) following brief digestion with trypsin/EDTA and low speed centrifugation. Hepatocyte cells express phenylalanine hydroxylase, and therefore can be selected in tyrosine free medium [Haggerty, D. F., P. L. Young, and J. V. Buese, A tyrosine-free medium for the selective growth of cells expressing phenylalanine hydroxylase activity. Dev Biol, 1975. 44(1): p. 158-68.]. The hepatocyte cells were plated on HEMA (poly 2-hydroxyethyl methacrylate) plates in tyrosine free modified IMEM (Modified Improved Essential Medium) obtained from Sigma-Aldrich (St. Louis, Mo.) [See, Gopalakrishnan, T. V. and W. F. Anderson, Epigenetic activation of phenylalanine hydroxylase in mouse erythroleukemia cells by the cytoplast of rat hepatoma cells. Proc Natl Acad Sci USA, 1979. 76(8): p. 3932-6.], supplemented with 5% dialyzed fetal bovine serum (SAFC), ITS (Insulin, transferrin, and selenium, obtained from Sigma, St. Louis, Mo.), 10 ng/ml each of epidermal growth factor (EGF) and basic fibroblast growth factor (bFGF) obtained from PeproTech, Rocky Hill, N.J., 08553, mM nicotinamide (Sigma, St. Louis, Mo.), gentamicin, and fungizone, referred to as TIEFNA medium, for several days. The cells were collected and triturated well and used for fusion with either functionally enucleated E14TG. Approximately 3-5 million functionally enucleated cells were mixed with 2-3 million primary hepatocyte cells and suspended vigorously to obtain a mixed population of cells. The mixed population of cells were centrifuged at 1500 rpm in a table top centrifuge. The cell pellet was suspended in 0.5 ml of concanavalin-A solution in DPBS (100 ug/ml final concentration) and incubated at room temperature for five minutes with intermittent mixing to obtain a suspension of cells. The suspension of cells was centrifuged and the supernatant was aspirated thoroughly. The cell pellet was suspended in 0.1-0.2 ml of 30% PEG (polyethylene glycol) (PEG1450, obtained from Sigma-Aldrich) solution by gentle trituration and incubated at room temperature for 3-4 minutes. The cell suspension was diluted with 5 ml of DF5 (50/50 DMEM/F12 supplemented with 5% FBS and antibiotics) medium and centrifuged. The cells were then plated on HEMA plates in TIEFNA medium.

While the selection method was being standardized, it was noted that many cells attached when the cells were plated on tissue culture or on Basement Membrane Extract, (BME obtained from Trevigen, Gaithersburg, Md. 20877) coated plates immediately after fusion. The attached cells consisted of some hepatocytes as well as fibroblast like cells. These attached cells somehow interfered in the development of pure population of hepatocyte cell lines. Therefore, the fused cells were kept under selective medium on HEMA plates until a growing population emerged. Once these cells were selected fully in TIEFNA medium, the cells grew only as a floating population of clusters and did not attach either to regular or BME coated dishes. These cells looked like pure population of freshly isolated hepatocytes. The cells were then maintained in TIEFD (in tyrosine free modified IMEM [Gopalakrishnan, T. V. and W. F. Anderson, Epigenetic activation of phenylalanine hydroxylase in mouse erythroleukemia cells by the cytoplast of rat hepatoma cells. Proc Natl Acad Sci USA, 1979. 76(8): p. 3932-6.], (obtained from Sigma-Aldrich) supplemented with 5% dialyzed fetal bovine serum (SAFC), ITS (Insulin, transferrin, and selenium, [Sigma]), 10 ng/ml each of EGF and bFGF (PeproTech, Rocky Hill, N.J., 08553), 0.1 uM dexamethasone (Sigma), gentamicin, and fungizone) medium.

Example 8

Epigenetic Induction of Hepatocyte Phenotype in Adult Human Cells

Human hepatocyte cell line, HFL-140 (see Example No. 1), was used as cytoplasmic donor cells to develop EIH cell lines from valproic acid treated adult human PBMNC and fibroblast cells. Functionally enucleated cells were fused with valproic acid treated cells as described before. Cells were plated on HEMA plates in DIEF medium (DF5 medium supplemented with ITS, and 10 ng/ml each of EGF and bFGF) for 24 hrs, centrifuged and plated on regular tissue culture plates in the same medium. The cells were maintained in this medium for up to 10 days. The cells were then plated in TIEFD (tyrosine free medium with ITS, EGF, and bFGF, and 0.1 uM dexamethasone) medium. Actively growing populations of cells were obtained 4-5 weeks after fusion. The cells were then maintained in TIEFD medium.

Example 9

Human Pancreatic Beta Cell Line

Pancreatic beta cells were isolated from fetal pancreas tissue obtained from Advanced Biosciences Resources, Inc. (Alameda, Calif. 94501) as floating clusters following digestion of the fetal pancreas tissue with trypsin/EDTA. The cells were used immediately after isolation for fusion with functionally enucleated E14TG. Approximately 3-5 million functionally enucleated mouse ES cells were mixed with 1-2 million primary pancreatic beta cells and centrifuged at 1500 rpm in a table top centrifuge. The cell pellet was suspended in 0.5 ml of concanavalin A solution in DPBS (100 ug/ml final concentration) and incubated at room temperature for five minutes with intermittent mixing. The suspended cells were centrifuged and the supernatant was aspirated thoroughly. The cell pellet was suspended in 0.1-0.2 ml of 30% PEG by gentle trituration and incubated at room temperature for 3-4 minutes. The cell suspension was diluted with 5 ml of DF5 (50/50 DMEM/F12 supplemented with 5% FBS and antibiotics) and centrifuged. The cell pellet was suspended in DF5 medium and the cells were then plated on HEMA plates in DIEF (DF5 medium supplemented with, ITS (Sigma), 10 ng/ml each of human EGF and basic FGF, and antibiotics) medium with 0.1 uM for dexamethasone (DIEFD medium) for 4-5 days. The cells were then plated on tissue culture dishes in the same medium. Actively growing population of cells were selected and used for further studies. The cell line FP-30A was isolated in this manner. Functionally enucleated FP-30A cells were fused with primary pancreatic beta cells, FP-31 control, to generate the beta cell line, FP-31A.

Example 10

Epigenetic Induction of Pancreatic Beta Cell Phenotype in Adult Human Cells

Human pancreatic beta cell lines, FP-30A and FP-31A, were used as cytoplasmic donor cells to develop epigenetically induced pancreatic beta (EIPB) cell lines from valproic acid treated adult human PBMNC, A1749, and adult human fibroblast, 4299.

Functionally enucleated cytoplasmic donor pancreatic beta cell lines, FP-30A and FP-31A, were fused with valproic acid treated cells as described in Example No. 2. After fusion, the cells that underwent fusion were plated on HEMA plates in DIEF medium for 24 hrs, centrifuged and plated on regular tissue culture plates in the same medium. The cells that underwent fusion were maintained in this medium for up to 3-4 weeks to obtain EIPB cells from valproic acid treated adult human fibroblasts, 4299. These cells that underwent fusion were then grown in DIEFD medium. Actively growing population of EIPB cells from valproic acid treated PBMNC, A1749, appeared a couple of weeks later compared to fibroblasts, and these cells grew only in suspension. Also, the frequency of generation of EIPB cells from PBMNC was much lower compared to that of fibroblasts.

Example 11

Human DA Neuron Cell Line

Human neuronal cells were isolated from fetal brain tissue obtained from Advanced Biosciences Resources, Inc. (Alameda, Calif. 94501). The fetal brain tissue was triturated well in serum free medium and treated with trypsin/EDTA (Mediatech, Inc., Manassas, Va. 20109) for five minutes at 37° C. The trypsinzed cells were centrifuged in a table top centrifuge at 1500 rpm. The cell pellet was suspended and grown in DF5 medium supplemented with ITS (Sigma) for 10 days on tissue culture dishes. The cells were then grown in tyrosine free modified IMEM (Sigma-Aldrich) [Breakefield, X. O. and M. W. Nirenberg, Selection for neuroblastoma cells that synthesize certain transmitters. Proc Natl Acad Sci USA, 1974. 71(6): p. 2530-3.] supplemented with 5% dialyzed FBS, and 10 ng/ml each of human EGF and basic FGF, and ITS (TIEF medium) for 4-5 weeks to obtain primary DA neuronal cells.

The primary DA neuronal cells were used for fusion with functionally enucleated mouse ES cells, E14TG. Approximately 3-5 million functionally enucleated mouse ES cells were mixed with 2-3 million primary DA neuronal cells and centrifuged at 1500 rpm in a table top centrifuge. Following centrifugation, the cell pellet was suspended in 0.5 ml of concanavalin-A solution in DPBS (100 ug/ml final concentration) and incubated at room temperature for five minutes with intermittent mixing. The cell suspension was centrifuged and the supernatant was aspirated thoroughly, and, the cell pellet was suspended in 0.1-0.2 ml of 30% PEG (PEG1450, Sigma-Aldrich) by gentle trituration and incubated at room temperature for 3-4 minutes. The resulting cell suspension was diluted with 5 ml of DF5 medium and centrifuged. The cells from the pellet were then plated on HEMA plates in DIEF (DF5 medium supplemented with ITS and 10 ng/ml each of human EGF and basic FGF) for 24 hours. The cells that underwent fusion and grown for 24 hours were then collected and plated on regular tissue culture plates or on Basement Membrane Extract, BME (Trevigen, Gaithersburg, Md. 20877) coated plates in TIEF medium for several weeks until an actively growing population of cells is obtained. DAN-47A was developed by this method. Similarly, other DA neuron cell lines have also been developed.

Example 12

Epigenetic Induction of DA Neuron Phenotype in Adult Human Cells

Human DA cell line DAN-47A was used as cytoplasmic donor cells to generate epigenetically induced dopaminergic neuron (EIDN) cells from valproic acid treated adult human PBMNC, A1749, and adult human fibroblasts, 4299.

Functionally enucleated cytoplasmic donor dopaminergic neuron cell line DAN-47A was fused with valproic acid treated fibroblasts, 4299, and PBMNC, A1749 cells as described before in Example No 3. Following fusion, the cells were plated on HEMA plates in DIEF medium for 24 hrs, centrifuged and plated on regular tissue culture plates in the same medium. The cells were maintained in this medium for up to 3-4 weeks to obtain EIDN cells, EIDN-3AFb, from valproic acid treated fibroblasts, 4299. These EIDN cells were tested for their ability to grow in tyrosine free medium. The EIDN cells grew well in this medium. Actively growing population of EIDN cells, EIDN-4, from valproic acid treated PBMNC, A1749, appeared several weeks later and with a much lower frequency, and grew much more slowly compared to EIDN cells from fibroblasts.

Example 13

STR Analysis (Finger Printing)

STR analysis was performed by Cell Line Genetics, Madison, Wis., 53719. Cell pellets of cytoplasmic donor hepatocyte cell line, HFL-140, EIH cell lines (EIH-1Fb, and EIH-4), cytoplasmic donor pancreatic beta cell lines (FP-30A and FP-31A), EIPB cell lines (EIPB-2Fb and EIPB-3), DA neuron cell lines (DAN-47A), EIDN cell lines (EIDN-3AFb and EIDN-4), PBMNC cells (A1749, PCA1584), and human fibroblast cells (4299) were sent to the company. Final report of STR analysis was provided by the company. The cells were analyzed for sixteen genetic loci for repetitive sequences, and the prevalence of repetitive sequence is compared to identify the cells.

Example 14

Immunostaining

Since the hepatocyte cytoplasmic donor cell line, HFL-140, and the EIH cell lines, EIF-1Fb and EIH-4, grew only in suspension, the cells were plated over a mitotically arrested human fibroblast cells. The fibroblast cells were coated with Con A for about 5 minutes, excess ConA removed and the hepatocyte and EIH cells were then added. The cells attached fairly tightly to Con A treated fibroblast cells. The cells were incubated for about 10 minutes, and were then fixed with 4% paraformaldehyde for 20 minutes at room temperature, and then permeabilized with cold methanol for 5 minutes. DA neuron cell line, DAN-47A, and the EIDN cell lines, EIDN-3AFb and EIDN-4, were grown on 24 well plates in regular growth medium. The cells were then fixed with 4% paraformaldehyde for 20 minutes at room temperature, and then permeabilized with cold methanol for 5 minutes. The fixed cells were blocked with 2.5% horse serum for 20 minutes at room temperature. The cells were then treated with appropriate antibodies for: Phenylalanine hydroxylase, alpha-1 antitrypsin, albumin, CYP3A4, insulin, peptide C, PDX-1, Glut-2, tyrosine hydroxylase, beta tubulin III, Nurr1, and Pitx-3 (Santa Cruz Bio Technology, Santa Cruz, Calif., 95060) for one hour at room temperature followed by incubation with enzyme conjugated secondary antibody (Peroxidase conjugated ImmPress Anti-Mouse IgG and Anti-Goat IgG Kits obtained from Vector laboratories, Burlingame, Calif., 94010). The cells were then treated with Vector NovaRED or ImmPACT DAB substrate, as recommended by the vendor, Vector laboratories. The antibody stained cells were counterstained with hematoxylin (Vector Laboratories), and the images were captured by AMG EVOS microscope (AMG, Mill Creek, Wash. 98012).

Example 15

Materials, Methods, and Results

Cells: The following human cancer cell lines were obtained from ATCC:—human hepatoma, Hep G2 (ATCC#HB-8065); human colorectal carcinoma, T-84 (ATCC # CCL-248); Burkitt lymphoma, Daudi (ATCC# CCL-213); and T-Cell leukemia, Jurkat (ATCC# TIB-152). The cells were grown in 50/50DMEM/F12 (Mediatech) supplemented with 5% fetal bovine serum (FBS), gentamicin and fungizone (DF5 medium).

Functional enucleation of cells: Functional enucleation of human cancer cell lines was carried out using modifications of a previously published method [Gopalakrishnan, T. V. and J. W. Littlefield, RNA from rat hepatoma cells can activate phenylalanine hydroxylase gene of mouse erythroleukemia cells. Somatic Cell Genet, 1983. 9(1): p. 121-31.]. It was shown in these studies that treatment of cells with a high concentration of mitomycin C completely prevents contribution of single selectable gene marker necessary for the survival of hybrids following fusion with a partner cell deficient in the same selectable marker gene. Mitomycin C treatment brings about activation of nucleases that cause the destruction of nuclear DNA. Different cell types were treated with 100 ug/ml of mitomycinC (Sigma-Aldrich) for three hours in suspension. The cells were collected by centrifugation and rinsed three times with HBSS, and used immediately for fusion.

Human hepatocyte cell line: Fetal liver hepatocyte cells were isolated from fetal liver tissue (Advanced Biosciences Resources, CA) following brief digestion with trypsin/EDTA and low speed centrifugation. Adult hepatocyte cells were obtained from InVitrogen. Both fetal liver and adult liver hepatocyte cells express phenylalanine hydroxylase, and therefore can be selected in tyrosine free medium [Gopalakrishnan, T. V. and W. F. Anderson, Epigenetic activation of phenylalanine hydroxylase in mouse erythroleukemia cells by the cytoplast of rat hepatoma cells. Proc Natl Acad Sci USA, 1979. 76(8): p. 3932-6]. The cells were plated on HEMA plates in tyrosine free modified IMEM [Haggerty, D. F., P. L. Young, and J. V. Buese, A tyrosine-free medium for the selective growth of cells expressing phenylalanine hydroxylase activity. Dev Biol, 1975. 44(1): p. 158-68.], (obtained from Sigma-Aldrich) supplemented with 5% dialyzed fetal bovine serum (SAFC), 10 ng/ml each of EGF and bFGF (PeproTech), 10 mM nicotinamide (Sigma), gentamicin, and fungizone (TEFNA medium) for several days. The cells were collected and triturated well and used for fusion separately with functionally enucleated HepG2, T-84, Daudi, and Jurkat cell lines. Approximately 3-5 million functionally enucleated cells were mixed with 2-3 million primary hepatocyte cells and suspended vigorously. The cells were centrifuged at 1500 rpm in a table top centrifuge. The cell pellet was suspended in 0.5 ml of concanavalin-A (Sigma-Aldrich) solution in DPBS (100 ug/ml final concentration) and incubated at room temperature for five minutes with intermittent mixing. The cells were centrifuged and the supernatant was aspirated thoroughly. The cell pellet was suspended in 0.1-0.2 ml of 30% PEG (PEG1450, Sigma-Aldrich) solution by gentle trituration and incubated at room temperature for 3-4 minutes. The cell suspension was diluted with 5 ml of DF5 medium and centrifuged. The cells were then plated on HEMA plates in TEFNA medium. While the selection method was being standardized, it was noted that many cells attached when the cells were plated on tissue culture or on Basement Membrane Extract, (BME; Trevigen) coated plates immediately after fusion. This consisted of some hepatocytes as well as fibroblast like cells. These attached cells somehow interfered in the development of pure population of hepatocyte cell lines. Therefore, the fused cells were kept under selective medium on HEMA plates until a growing population emerged. Once these cells are selected fully in TEFNA medium, the cells grew only as a floating population of clusters and did not attach either to regular or BME coated dishes. These cells looked like pure population of freshly isolated hepatocyte cells.

Hepatocyte cell line H-910G was derived from fusion of normal adult hepatocyte cells by fusion with functionally enucleated human hepatoma cell line, HepG2. Hepatocyte cell lines H-147G, H-147J, H-147T, and H-147D were obtained by fusion of fetal hepatocyte cells with functionally enucleated human hepatoma, Jurkat, T-84, and Daudi cancer cell lines respectively. Hepatocyte cell lines H-146G and H-146D were obtained by fusion of fetal hepatocyte cells with functionally enucleated human hepatoma and Daudi cancer cell lines respectively.

The hepatocyte cell lines were tested for the expression of the following hepatocyte cell specific marker genes: Albumin, alpha1-anti trypsin, phenylalanine hydroxylase, and cytochrome P450 CYP3A4. The expression of these marker genes in the epigenetically induced hepatocyte cell lines was very similar to the level of expression in both adult liver and fetal liver hepatocyte cells.

Human pancreatic beta cell line: Pancreatic beta cells were isolated from fetal pancreas tissue (Advanced Biosciences Research, CA) as floating clusters following digestion with trypsin/EDTA. The cells were used immediately after isolation for fusion with functionally enucleated Daudi human cancer cell line. Adult pancreatic islet cells were obtained from NDRI, NJ. Both adult and fetal pancreatic cells (1-2 million cells for each) were fused with approximately 3-5 million functionally enucleated human cancer cells, Hep G2 and Daudi respectively. The cells were mixed and centrifuged at 1500 rpm in a table top centrifuge. The cell pellet was suspended in 0.5 ml of concanavalin A (Sigma-Aldrich) solution in DPBS (100 ug/ml final concentration) and incubated at room temperature for five minutes with intermittent mixing. The cells were centrifuged and the supernatant was aspirated thoroughly. The cell pellet was suspended in 0.1-0.2 ml of 30% PEG (PEG1450, Sigma-Aldrich) by gentle trituration and incubated at room temperature for 3-4 minutes. The cell suspension was diluted with 5 ml of DF5 medium and centrifuged. The cells were then plated on HEMA plates in DEFNA (DF5 medium supplemented with, 10 ng/ml each of human EGF and basic FGF, 10 mM nicotinamide, and antibiotics) medium. The cells were maintained on HEMA plates until actively growing population of cells were obtained. The cells were then plated on tissue culture dishes in the same medium. Pancreatic beta cell lines Isl-311D was obtained by fusion of adult pancreatic beta cells with functionally enucleated human cancer cells, Hep G2. Pancreatic beta cell line FP-37D was obtained by fusion of fetal pancreatic cells with functionally enucleated human cancer cell line, Daudi.

The pancreatic beta cells lines were tested for the production of insulin by ELISA assay using commercially available human ELISA kits (EMD). The cell lines produced increasing amount of insulin with increasing concentration of glucose. The cell lines also expressed pdx-1, peptide C, and Glut-2 as tested by immunostaining.

Human dopaminergic (DA) neuron cell line: Human neuronal cells were isolated from fetal brain tissue (Advanced Biosciences Research, CA). Brain tissue was triturated well in serum free medium and treated with trypsin/EDTA (Mediatech) for five minutes at 37 C. The cells were spun and grown in DF5 medium supplemented with ITS (Sigma) for 10 days on tissue culture dishes. The cells were then grown in tyrosine free modified IMEM (Sigma-Aldrich) supplemented with 5% dialyzed FBS, and 10 ng/ml each of human EGF and basic FGF, and ITS (TIEF medium) for 4-5 weeks to obtain primary DA neuronal cells. They were used for fusion with functionally enucleated human cancer cell line, Daudi. Approximately 3-5 million functionally enucleated Daudi cells were mixed with 2-3 million primary DA neuronal cells and centrifuged at 1500 rpm in a table top centrifuge. The cell pellet was suspended in 0.5 ml of concanavalin-A (Sigma-Aldrich) solution in DPBS (100 ug/ml final concentration) and incubated at room temperature for five minutes with intermittent mixing. The cells were centrifuged and the supernatant was aspirated thoroughly. The cell pellet was suspended in 0.1-0.2 ml of 30% PEG (PEG1450, Sigma-Aldrich) by gentle trituration and incubated at room temperature for 3-4 minutes. The cell suspension was diluted with 5 ml of DF5 medium and centrifuged. The cells were then plated on HEMA plates in DIEF (DF5 medium supplemented with ITS and 10 ng/ml each of human EGF and basic FGF) for 24 hours. The cells were then plated on regular tissue culture plates or on Basement Membrane Extract, BME (Trevigen) coated plates in TIEF medium for several weeks until an actively growing population of cells was obtained. DAN-43D was developed by this method.

The dopaminergic neuron cell line, DAN-43D, was tested for the expression of tyrosine hydroxylase, beta tubulin III, Nurr1, and Pitx-3 by immunostaining. The cell line expressed all the dopaminergic neuron specific markers.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A method of preparing a self-propagating pancreatic beta cell specific to a human patient, the method comprising:
   (a) obtaining a human cancer cell;
   (b) treating the human cancer cell with a DNA interchelating agent to obtain a DNA interchelating agent treated human cancer cell;
   (c) treating the DNA interchelating agent treated human cancer cell with an agglutinin to obtain an agglutinin-treated human cancer cell;
   (d) fusing the agglutinin-treated human cancer cell from step (c) with a human pancreatic beta cell to obtain a self-propagating human pancreatic beta cytoplasmic donor cell, wherein the human pancreatic beta cell comprises a cell from a human adult pancreas;
   (e) treating the self-propagating human pancreatic beta cytoplasmic donor cell from step (d) with a DNA interchelating agent to obtain a DNA interchelating agent treated human pancreatic beta cytoplasmic donor cell;
   (f) treating the DNA interchelating agent treated human pancreatic beta cytoplasmic donor cell from step (e) with an agglutinin to obtain an agglutinin-treated human pancreatic beta cytoplasmic donor cell;
   (g) fusing the agglutinin-treated human pancreatic beta cytoplasmic donor cell from step (f) with a histone deacetylase inhibitor treated cell from a human patient whereby a self-propagating pancreatic beta cell specific to the human patient is obtained, and wherein the histone deacetylase inhibitor treated cell from the human patient is obtained by treating a cell from the human patient with a histone deacetylase inhibitor.

2. The method of claim 1, the human cancer cell is a human hepatoma cell, a human colorectal carcinoma cell, a Burkitt lymphoma cell, a Burkitt lymphoma cell, or a T-cell leukemia cell.

3. The method of claim 1, wherein the DNA interchelating agent is mitomycin C, ethidium bromide, or DAPI.

4. The method of claim 1, wherein the agglutinin is concanavalin A, phytohemagglutinin, or wheat germ lectin.

5. The method of claim 1, wherein a tissue culture medium for growing the self-propagating pancreatic cell from step (d) comprises a complete tissue culture medium or a complete tissue culture medium comprising human EGF and human basic FGF.

6. The method of claim 1, wherein the histone deacetylase inhibitor is valproic acid, trichostatin A, or vorinostat.

7. The method of claim 1 comprising propagating the self-propagating pancreatic cell from step (d) to obtain, a human pancreatic cytoplasmic donor cell line.

8. The method of claim 1 comprising propagating the self-propagating pancreatic beta cell specific to the human patient to obtain a pancreatic beta cell line specific to the human patient.

9. The method of claim 1, wherein a tissue culture medium for growing the self-propagating pancreatic cell specific to the human patient from step (f) comprises a complete tissue culture medium or a complete tissue culture medium comprising human EGF and human basic FGF.

* * * * *